(12) United States Patent
Kakee et al.

(10) Patent No.: US 7,666,139 B2
(45) Date of Patent: Feb. 23, 2010

(54) ULTRASONIC IMAGING APPARATUS AND METHOD

(75) Inventors: Akihiro Kakee, Tochigi-ken (JP);
Makoto Hirama, Tochigi-ken (JP);
Tetsuya Kawagishi, Tochigi-ken (JP);
Tomohisa Imamura, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 537 days.

(21) Appl. No.: 10/682,733

(22) Filed: Oct. 10, 2003

(65) Prior Publication Data

US 2004/0133106 A1    Jul. 8, 2004

(30) Foreign Application Priority Data

Oct. 10, 2002   (JP)   ............................. 2002-296907
Jun. 10, 2003   (JP)   ............................. 2003-165023

(51) Int. Cl.
*A61B 8/00*   (2006.01)
*A61B 8/12*   (2006.01)
*A61B 8/14*   (2006.01)

(52) U.S. Cl. ...................... 600/443; 600/437; 600/440; 600/458

(58) Field of Classification Search ................. 600/440, 600/443, 458, 437
See application file for complete search history.

(56) References Cited

U.S. PATENT DOCUMENTS

| | | | |
|---|---|---|---|
| 5,379,642 A * | 1/1995 | Reckwerdt et al. | ............. 73/625 |
| 5,632,277 A | 5/1997 | Chapman et al. | |
| 5,706,819 A * | 1/1998 | Hwang et al. | ............... 600/458 |
| 5,833,613 A * | 11/1998 | Averkiou et al. | ............. 600/440 |
| 5,902,243 A * | 5/1999 | Holley et al. | ................. 600/443 |
| 6,186,950 B1 * | 2/2001 | Averkiou et al. | ............. 600/443 |
| 6,425,869 B1 * | 7/2002 | Rafter et al. | ................. 600/458 |

FOREIGN PATENT DOCUMENTS

| | | |
|---|---|---|
| JP | 2001-286472 | 10/2001 |
| JP | 2002-165796 | 6/2002 |

OTHER PUBLICATIONS

Abiru, Iwao, Kamakura, Tomoo, Nonlinear Propagation of a Pulsed Ultrasound, University of Electro-Communications, US89-23, p. 53-60, 1989.

* cited by examiner

*Primary Examiner*—Brian Casler
*Assistant Examiner*—James Kish
(74) *Attorney, Agent, or Firm*—Oblon, Spivak, McClelland, Maier & Neustadt, L.L.P.

(57) ABSTRACT

An ultrasonic imaging apparatus, including an ultrasonic probe including an ultrasonic vibration element configured to transmit and receive an ultrasonic wave in a scanning direction in an object in which a contrast media has been injected; a transmission unit configured to apply successive drive pulses to the probe so as to transmit respective ultrasonic signals in respective rate sections; a reception unit configured to receive reflected ultrasonic signals, including first reflected ultrasonic signals produced by a first drive pulse in a first rate section and reflected back to the probe in the first rate section and in a second rate section subsequent to the first rate section; an operation unit configured to perform an operation including at least one of addition and subtraction of at least two of the first ultrasonic signals received during different rate sections; and a signal processor configured to produce image data based on the result of the operation performed by the operation unit. Plural driving pulses having alternating polarity may be applied to the probe in a same scan direction.

14 Claims, 22 Drawing Sheets

ULTRASONIC IMAGING APPARATUS AND METHOD

CROSS-REFERENCE TO RELATED APPLICATIONS

This application is based upon and claims the benefit of priority from prior Japanese Patent Applications No. 2002-296907 filed on Oct. 10, 2002 and No. 2003-165023 filed Jun. 10, 2003, the entire contents of which are incorporated herein by reference.

FIELD OF THE INVENTION

The present invention is related to an ultrasonic imaging apparatus that reduces a remaining echo to obtain a high resolution ultrasonic image with decreased artifact.

BACKGROUND OF THE INVENTION

A conventional ultrasonic imaging apparatus irradiates an ultrasonic wave generated from an ultrasonic vibration element in an ultrasonic probe to a patient, receives a reflected ultrasonic signal, by the ultrasonic probe, produced due to difference of sound impedance of tissue in the patient, and displays a ultrasonic image on a monitor. Since a 2-dimensional image is easily obtained in real time by putting the ultrasonic probe of the ultrasonic imaging apparatus on the patient, the ultrasonic imaging apparatus is widely used for morphologic diagnosis of various organs and functional diagnosis of a heart. In a conventional method of creating the ultrasonic image, an optimum ultrasonic frequency for a diagnostic part is selected, an ultrasonic wave pulse having a center frequency at the selected frequency is transmitted to the patient, and the reflective ultrasonic wave signal of almost equal to the center frequency is received to obtain the ultrasonic image.

In the meantime, a tissue harmonic imaging method (hereafter referred to as THI) has recently been developed, and the THI method spreads widely. The THI method uses a phenomenon of nonlinear ultrasonic propagation in a tissue. For example, when an ultrasonic wave of a center frequency (fo) is irradiated to a patient, a second harmonic component at twice the center frequency (2fo) is newly generated according to the phenomenon and is received by the ultrasonic probe with the basic ultrasonic wave at frequency (fo). A cause of generation of the harmonic component is that propagation speed of the ultrasonic wave pulse in the patient depends on sound pressure of the ultrasonic wave. For this reason, distortion of a received signal occurs and the harmonic component is generated. Generation of the harmonic component depends on status of the tissue, propagation distance to a reflective portion and ultrasonic intensity on the reflective portion. The dependence on the ultrasonic intensity can theoretically reduce generation of a side lobe which causes artifact on the ultrasonic image. Thus, using the THI method, a high resolution image can be obtained. It is difficult to appropriately extract the harmonic component from the received ultrasonic wave signal also including the basic component by a general filtering method, since parts of each of the frequency components overlap when each component has a wide frequency band.

As a method for extracting the harmonic component of wide frequency band, a pulse subtraction method has been developed, as described at page 53 of the 1989 publication by Ahirui et al., "Nonlinear Propagation of a Pulsed Ultrasound," Shingaku-giho, University of Electro-Communications, US 89-23, pp. 53-60, 1989. In the pulse subtraction method, two ultrasonic wave pulses having different polarity are transmitted in a predetermined direction, and received signals are added to reduce the basic component and extract the harmonic component. The pulse subtraction method is based on the fact that the harmonic component is generated in proportion to the square value of the amplitude of the basic component. Therefore, when the transmitted ultrasonic pulse is reversed, the basic component is also reversed, but the harmonic component is not reversed. In the pulse subtraction method, in order to acquire the different polarity signals from the same portion in a time interval which it takes to transmit and receive a single ultrasonic wave (one rate section). For this reason, it is desirable that the reflective portion is still within the one rate section in order to appropriately reduce the basic component. Therefore, when the pulse subtraction method is applied to an actual patient, the basic component remains due to a motion of internal organs or a body, and so-called motion artifact occurs. To address such a problem, Japanese Patent Publication (Kokai) No. 2002-165796 (P. 4, FIGS. 2 through 5) discloses a method for reducing the remaining harmonic component that still remains even after the pulse subtraction by combining the pulse subtraction method and the filtering method. Japanese Patent Publication (Kokai) No. 2001-286472 (P. 5, FIGS. 6 through 9) discloses another method for reducing the remaining harmonic component by detecting the amount of movement of the body based on the received signals during a single rate section and by adding the signals corrected based on the amount of the movement.

Meanwhile, in ultrasonic diagnosis of a heart or an abdomen, a method for obtaining status of blood flow by detecting a reflective ultrasonic wave from an ultrasonic contrast media (hereafter referred to as contrast media) injected into a blood vessel, is known. As the contrast media, micro bubbles are generally used. Although a big reflective wave on the micro bubbles can be relatively obtained since an ultrasonic reflective coefficient of the micro bubbles is larger than that of the blood, the micro bubbles can be easily broken by irradiating an ultrasonic wave of usual energy. However, it is not desirable to use bubbles hard to be broken or to repeatedly use the micro bubbles, because such the use can impose much burden on the patient. Thus, it is difficult to observe for a while the status of the blood flow, since the contrast media using the micro bubbles disappears in a short time upon ultrasonic irradiation. To address such a problem, Japanese Patent Publication (Kokai) No. 8-336527 (pp. 3-5, FIGS. 1 through 3) discloses that the reflected wave on the contrast media is appropriately extracted by subtracting two received signals acquired when two kinds of ultrasonic waves are transmitted to and received from the same position of the patient. According to this method, a 1st ultrasonic transmission and reception is performed. At this time, a part of the ultrasonic pulse is reflected on the contrast media, and a 1st ultrasonic reflected wave is obtained. On the other hand, all or part of the contrast media where the ultrasonic pulse is reflected is broken. For this reason, when a 2nd ultrasonic transmission and reception is subsequently performed, the ultrasonic reflected wave on the contrast media (contrast media component) is smaller than that of the 1st transmission and reception, and the ultrasonic reflected wave on the tissue of the patient (tissue component) is the same size as that of the 1st transmission and reception. Therefore, when the subtraction is performed between the 1st ultrasonic reflective wave and the 2nd ultrasonic reflective wave, the contrast media component is extracted.

When an ultrasonic transceiver cycle (herein referred to as rate cycle) is shortened in order to reduce the motion artifact and to the improve real-time characteristic of the image by the increasing frame rate (number of images displayed per second), before the reflected ultrasonic wave that is reflected in a deep portion is received by the ultrasonic probe, the next ultrasonic pulse is irradiated. In this situation, if the pulse subtraction or the imaging of the contrast media is performed, the artifact remains since the ultrasonic reflected waves obtained by different ultrasonic transmission and reception are overlapped within the one rate cycle.

FIG. 1A and FIG. 1B show illustrations for explaining an artifact generated when the rate cycle Tr is shortened. A reflector 1 is the tissue of the patient, a reflector 2 is the contrast media, and a reflector 3 is the tissue of the patient. It takes longer to perform transmission and reception of the reflector 3 than the rate cycle Tr. In the case of a sector scan, the transmission and reception of a first scanning direction is performed in the rate section (1) and rate section (2), and the transmission and reception of a second scanning direction that is adjacent to the first scanning direction is performed in the rate section (3) and rate section (4) as shown in FIG. 1A. FIG. 1B shows a rate pulse for determining an irradiation timing of the ultrasonic wave, received signals from the reflector 1, 2 and 3, and results of subtraction between received signals obtained in the rate sections (1) and (2) and between received signals obtained in the rate section (3) and (4). The size of the received signal is indicated as size of arrow.

That is, the ultrasonic pulse irradiated in the scanning direction θ1 in rate section (1) is reflected on a reflecting point A1 of the reflector 1, a reflecting point A2 of the reflector 2, and a reflecting point A3 of the reflector 3. The reflected ultrasonic waves are detected by the ultrasonic probe 1 as the reflected intensities a11 through a31. Subsequently, the ultrasonic pulse irradiated in the same scanning direction θ1 in the rate section (2) is reflected on the reflecting points A1 through A3, and received signals of reflective intensities a12 through a32 are acquired. In this case, before the ultrasonic pulse of the rate section (1) reflects at the reflecting point A3 and is received by the ultrasonic probe 1, the ultrasonic pulse of rate section (2) is irradiated. For this reason, the reflected ultrasonic wave from the reflected point A3 of the rate section (1) is detected together with the reflective ultrasonic wave from the reflection points A1 and A2 of the rate section (2). Therefore, as shown in FIG. 1B, when the subtraction between the received signals of the rate section (1) and (2) is performed, the received signal from the reflector A1 is reduced, but the received signal from the reflector A3 remains. The reflective ultrasonic wave that remains like the above reflective ultrasonic wave from the reflector A3 is called a remaining echo.

On the other hand, the size a22 of the received signal from the contrast media obtained in the rate section (2) is remarkably reduced in comparison with the size a21 of the received signal of the rate section (1) since the contrast media is broken in the rate section (1). For this reason, amount of change a21−a22 is detected by the subtraction between the received signal from the contrast media in rate section (1) and the received signal from the contrast media in the rate section (2). When the subtraction, as well as the rate section (1) and (2), is performed between the received signals acquired in the rate section (3) and (4), the ultrasonic wave of the size a32−b31 based on the change of the remaining echo and the ultrasonic wave of the size b21−b22 are detected. Since the reflecting point B3 is different from the reflecting point A3, generally A32≠b31 and the remaining echo exists as well.

SUMMARY OF THE INVENTION

One object of the present invention is to ameliorate the above-mentioned problems. To that end, according to one aspect of the present invention, there is provided an ultrasonic imaging apparatus, including an ultrasonic probe including an ultrasonic vibration element configured to transmit and receive an ultrasonic wave in a scanning direction in an object in which a contrast media has been injected; a transmission unit configured to apply successive drive pulses to the probe so as to transmit respective ultrasonic signals in respective rate sections; a reception unit configured to receive reflected ultrasonic signals, including first reflected ultrasonic signals produced by a first drive pulse in a first rate section and reflected back to the probe in the first rate section and in a second rate section subsequent to the first rate section; an extraction unit configured to extract a contrast medium signal by performing at least one of addition and of the first reflected signals received during the first rate section and the subsequent rate section; and a signal processor configured to produce first image data based on the extracted contrast medium signal.

According to another aspect of the present invention, there is provided an ultrasonic imaging apparatus, including an ultrasonic probe including an ultrasonic vibration element configured to transmit and receive an ultrasonic wave in a scanning direction in an object in which a contrast media has been injected; a transmission unit configured to apply successive drive pulses to the probe so as to transmit respective ultrasonic signals in respective rate sections; a reception unit configured to receive reflected ultrasonic signals, including first reflected ultrasonic signals produced by a first drive pulse in a first rate section and reflected back to the probe in the first rate section and in a second rate section subsequent to the first rate section; an operation unit configured to perform an operation including at least one of addition and subtraction of at least two of the first ultrasonic signals received during different rate sections; and a signal processor configured to produce image data based on the result of the operation performed by the operation unit.

According to another aspect of the present invention, there is provided an ultrasonic imaging method, including applying successive drive pulses to a probe so as to transmit respective ultrasonic signals in respective rate sections; receiving reflected ultrasonic signals produced by a first drive pulse in a first rate section and reflected back to the probe in the first rate section and in a second rate section subsequent to the first rate section; performing an operation including at least one of addition and subtraction of at least two of the ultrasonic signals received during different rate sections; and producing image data based on the result of the operation.

According to another aspect of the present invention, there is provided an ultrasonic imaging apparatus, including an ultrasonic probe including an ultrasonic vibration element configured to transmit and receive an ultrasonic wave in a scanning direction in an object; a transmitter configured to apply to the ultrasonic vibration element N driving pulses, N>2, in the same scanning direction and to change a polarity of the driving pulses being applied in the same scanning direction alternately; a receiver configured to receive a plurality of ultrasonic signals from the vibration element; a harmonic extraction unit configure to extract a harmonic component based on the plurality of received ultrasonic signals;

and a signal processor configured to produce image data based on the harmonic component.

According to another aspect of the present invention, there is provided an ultrasonic imaging apparatus, including an ultrasonic probe including an ultrasonic vibration element configured to transmit and receive an ultrasonic wave in a scanning direction in an object; a transmitter configured to apply N driving pulses, where N>1, to the vibration element in the same scanning direction and to change a polarity of the driving pulses applied in the same scanning direction alternately; a receiver configured to receive from the vibration element a plurality of ultrasonic reflection signals produced by the N driving pulses in the same scanning direction in M rate sections, where M>2; a harmonic extraction unit configure to extract a harmonic component based on the ultrasonic signals received in the M rate sections; and a signal processor configured to produce image data based on the harmonic component.

According to another aspect of the present invention, there is provided an ultrasonic imaging apparatus, including an ultrasonic probe including an ultrasonic vibration element configure to transmit and receive an ultrasonic wave in a scanning direction in an object; means for applying to the ultrasonic vibration element N driving pulses, N>2, in the same scanning direction and for changing a polarity of the driving pulses being applied in the same scanning direction alternately; means for receiving a plurality of ultrasonic signals from the vibration element; means for extracting a harmonic component based on the plurality of received ultrasonic signals; and a signal processor configured to create image data based on the harmonic component.

According to another aspect of the present invention, there is provided an ultrasonic imaging apparatus, including an ultrasonic probe including an ultrasonic vibration element configure to transmit and receive an ultrasonic wave in a scanning direction in an object; a transmitter configured to apply N driving pulses, where N>2, to the vibration element in the same scanning direction and to change a polarity of the driving pulses applied in the same scanning direction alternately; a receiver configured to receive from the vibration element a plurality of ultrasonic reflection signals produced by the N driving pulses in the same scanning direction in M rate sections, where M>1; a harmonic extraction unit configure to extract a harmonic component based on the ultrasonic signals received in the M rate sections; and a signal processor configured to create image data based on the harmonic component.

According to another aspect of the present invention, there is provided an ultrasonic imaging method, including applying to an ultrasonic vibration element N driving pulses, N>2, in a same scanning direction and changing a polarity of the driving pulses being applied in the same scanning direction alternately; receiving a plurality of ultrasonic signals from the vibration element; extracting a harmonic component based on the plurality of received ultrasonic signals; and producing image data based on the harmonic component.

BRIEF DESCRIPTION OF THE DRAWINGS

A more complete appreciation of the invention and many of the attendant advantages thereof will be readily obtained as the same becomes better understood by reference to the detailed description when considered in connection with the accompanying drawings. In the drawings.

DETAILED DESCRIPTION OF THE INVENTION

Figure 1A:
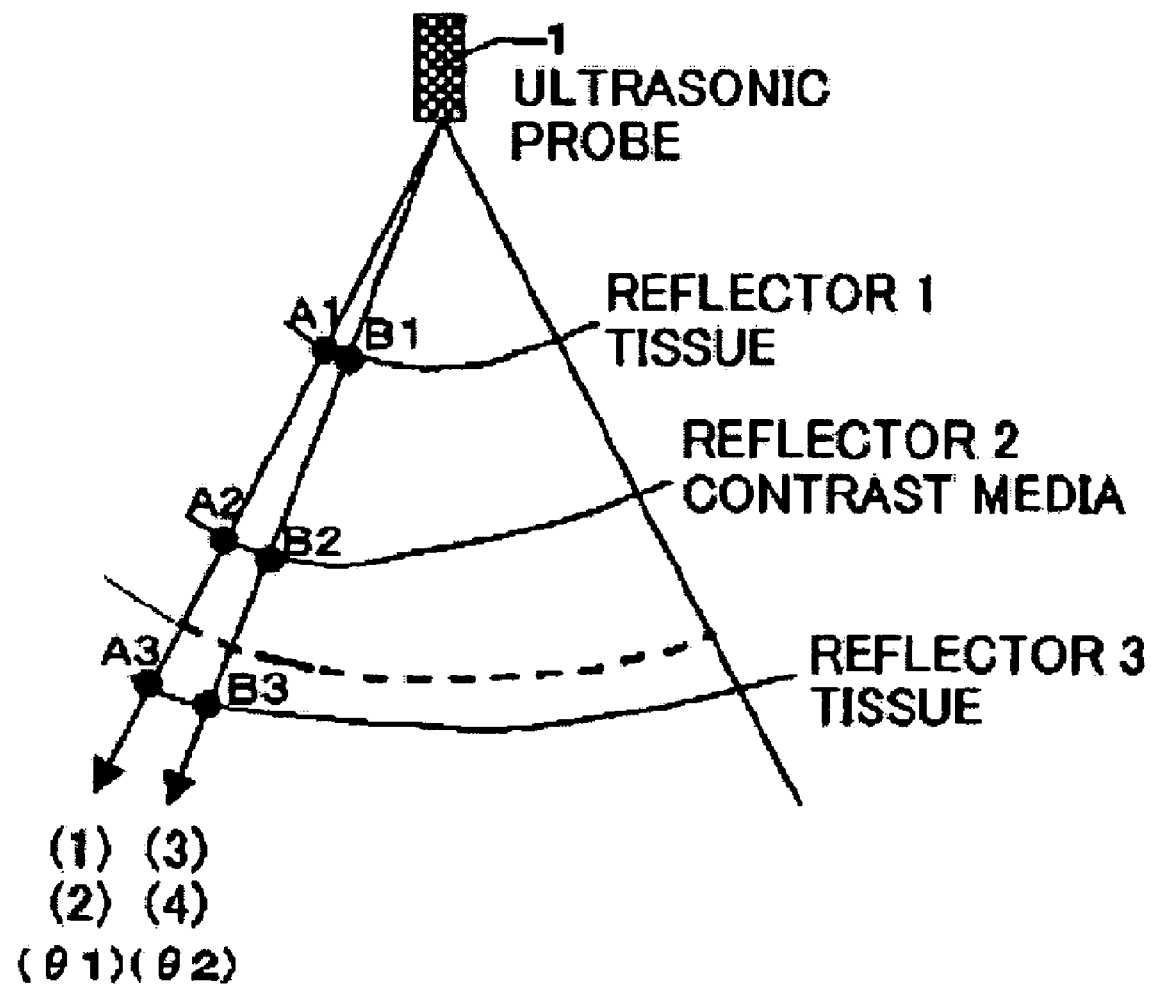
FIG. 1A and FIG. 1B are illustrations for explaining a remaining echo in a conventional method.
Figure 1B:
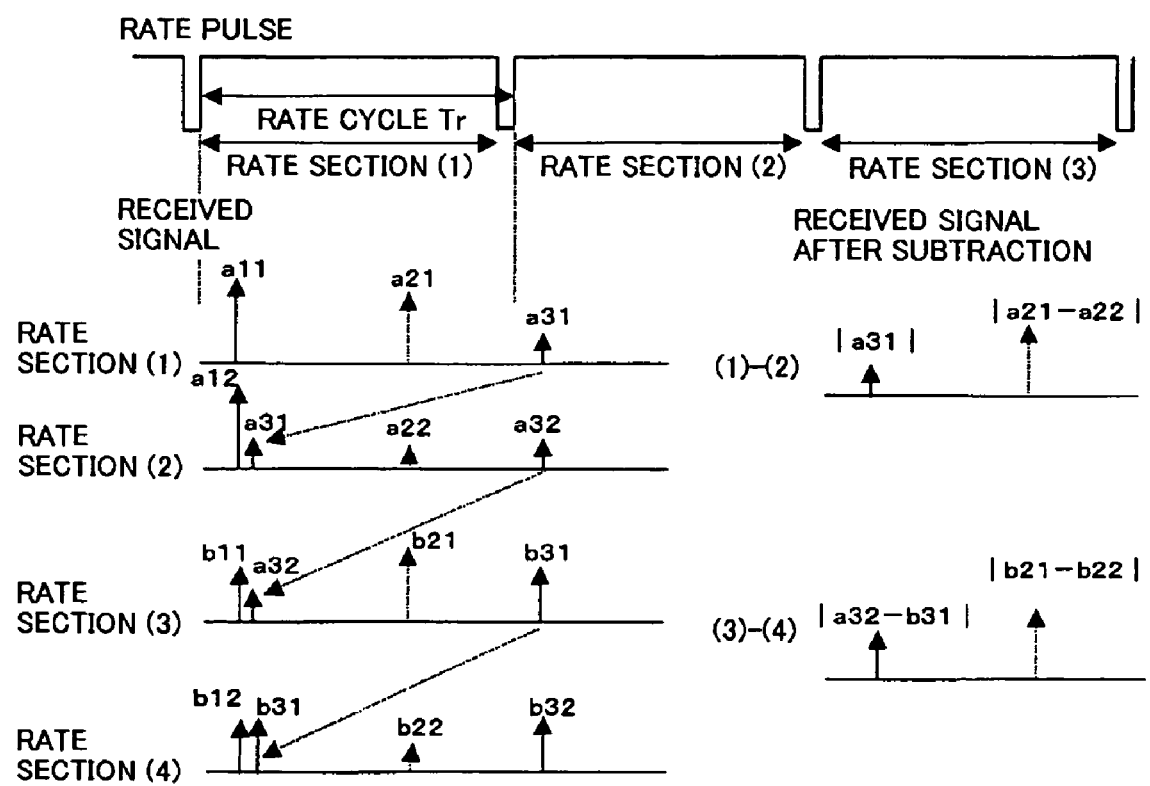

Referring now to the drawings, wherein like reference numerals designate the same or corresponding parts throughout the several views, a first embodiment is next explained.

First Embodiment

In THI method, the polarity of an ultrasonic wave is repeatedly tuned and transmission and reception is performed Nx times. A harmonic component is extracted by adding a received signal of (Nx−1)th transmission and reception to a received signal of (Nx)th transmission and reception.

Figure 2:
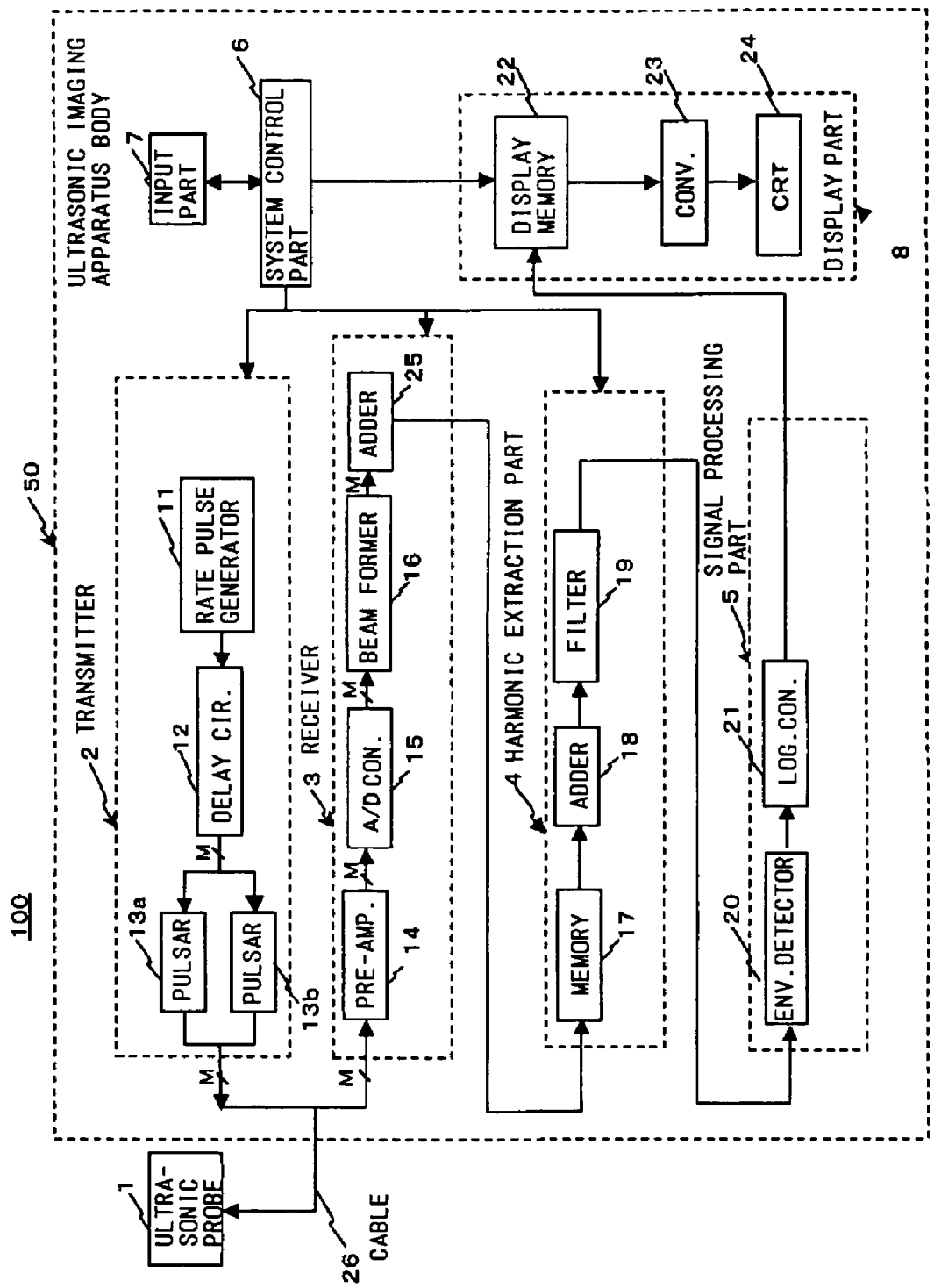
FIG. 2 is a block diagram of an ultrasonic imaging apparatus of a first embodiment and a second embodiment.

FIG. 2 is a block diagram of the ultrasonic imaging apparatus 100. The ultrasonic imaging apparatus 100 includes an ultrasonic probe 1 that transmits an ultrasonic pulse (transmitted ultrasonic wave) and changes a reflective ultrasonic wave (received ultrasonic wave) to a signal and includes an ultrasonic imaging apparatus body 50 that creates image data based on the received signal obtained by the ultrasonic probe. The ultrasonic imaging apparatus body 50 includes a transmitter 2 that transmits the ultrasonic pulse to a predetermined direction in a patient, a receiver 3 that receives the signal from the predetermined direction, a harmonic extraction part 2 that extracts a harmonic component from the signal, and a signal processing part 5 that performs signal processing for creating the image data. Further the ultrasonic imaging apparatus body 50 includes a display part 8 that stores the image data, converts the image data to TV signal and displays an ultrasonic image, a input part 7 by which an operator inputs various commands or transceiver conditions and a system controller 6 that controls each part. On the top of the ultrasonic probe 1, M ultrasound vibration elements are arranged on a single line. The vibration elements contact the patient to transmit and receive the ultrasonic wave. Each vibration element is connected to the transmitter 2 and the receiver 3 via a cable 26 including a plurality of signal lines. Each vibration element is an electric oscillation element, which converts an electric pulse to an ultrasonic pulse when the transmission is performed, and converts the returned ultrasonic pulse to an electric pulse when the reception is performed. The operator can arbitrarily select the ultrasonic probe 1 from a sector scan probe, a linear scan probe and a convex scan probe. The following explanation is of a case where the sectors can probe is selected.

The transmitter 2 of the ultrasonic imaging apparatus body 50 includes a rate pulse generator 11, a transmission delay circuit 12 and a pulsar 13. The rate pulse generator 11 generates a rate pulse that determines repeat cycle (rate cycle) of the ultrasonic pulse to the patient and provides the rate pulse to the transmission delay circuit 12. The transmission delay circuit 12 includes M channel delay elements. The number of the delay elements is equal to the number of the vibration elements. A focus delay time that determines a focal distance and a direction delay time that determines a direction are imposed on the rate pulse that is supplied to the pulsar 13. The pulsar 13 includes M channel driving elements that transmit the ultrasonic wave. The number of the driving elements is equal to the number of the delay elements of the transmission delay circuit 12. The pulsar 13 drives the ultrasonic vibration elements to transmit the ultrasonic wave. The pulsar 13 includes a pulsar 13a that generates a driving pulse of positive polarity and a pulsar 13b that generates a driving pulse of negative polarity, both driving pulses are generated based on an output signal from the transmission delay circuit 12. The driving pulse of the pulsar 13b is of opposite polarity to the driving pulse of the pulsar 13a.

The receiver 3 includes a pre-amplifier 14, an A/D converter 15, a beam former 16 and an adder 25. The pre-amplifier 14 amplifies the small electric signal received by the vibration element to establish appropriate S/N. The amplified signal including the basic component and the harmonic component is converted to a digital signal and is supplied to the beam former 16. The beam former 16 imposes a focus delay time for receiving the ultrasonic wave from a predetermined depth and a direction delay time for determining a receiving direction on the digital signal. The adder 25 performs a phase adjustment addition process to an output signal from the beam former 16. In the phase adjustment addition process, phases of the received signals are adjusted and are added. The harmonic extraction part 4 includes a waveform memory 17, an adder 18 and a filter circuit 19. The waveform memory 17 temporarily stores the received signals obtained by the (Nx−1)th transmission and reception in a predetermined direction. The adder 18 adds the received signal obtained by the Nth transmission and reception in the same direction to the received signal stored in the waveform memory 17 to reduce the basic component. The filter circuit 19 reduces a remaining basic component due to the motion of the internal organs or the body of the patient. The filter circuit 19 may be a band pass filer circuit (BPF) or a high pass filter circuit (HPF).

The signal processing part 5 includes an envelope detector 20 and a logarithmic converter 21. The signal processing part 5 processes an output signal from the harmonic extraction part 4 to create the image data. The envelope detector 20 detects an envelope curve of the inputted digital signal. The logarithmic converter 21 includes a look-up table for performing logarithmic process to an input signal. The logarithmic converter 21 relatively emphasizes a small signal by changing amplitude to logarithm. The received signal from the patient generally has a wide dynamic range of more than 80 dB. In order to display the received signal within 30 dB that is a dynamic range of a general TV monitor, for example, the received signal is compressed. The display part 8 includes a display memory 22, a converter 23 and a CRT monitor 24. The display memory 22 combines the image data supplied from the signal processing part 5 and information data, such as letter and number related to the image data, and temporarily stores the combined data. The stored image data and information data is D/A converted by the converter 23 and is displayed on the CRT monitor 24 as TV format signal. The input part 7 includes input devices, such as a liquid crystal display panel, a keyboard, a trackball, and a mouse, on an operation panel. The operator inputs patient information, transceiver condition, such as rate cycle Tr, and selection of image display mode. Also, a command for starting creation of the image in THI using the pulse subtraction, or a weighted coefficient K for setting transmission and reception time Nx is inputted.

The system control part 6 includes a CPU and a memory circuit, and controls each part of the whole system, such as the transmitter 2, the receiver 3, the harmonic extraction part 4, and the display part 8, based on instruction signal(s) from the input part 7. In the first embodiment, the system control part 6 sends control signal for changing the polarity of ultrasonic wave pulses by the pulsar 13 to the transmitter 2. The system control part 6 sends a control signal for determining a filter characteristic, such as a center frequency and a frequency band of the filter circuit 19 and a control signal for controlling the waveform memory 17 and the adder 18 to the harmonic extraction part 4.

(Creation of Image Data)

Figure 3:
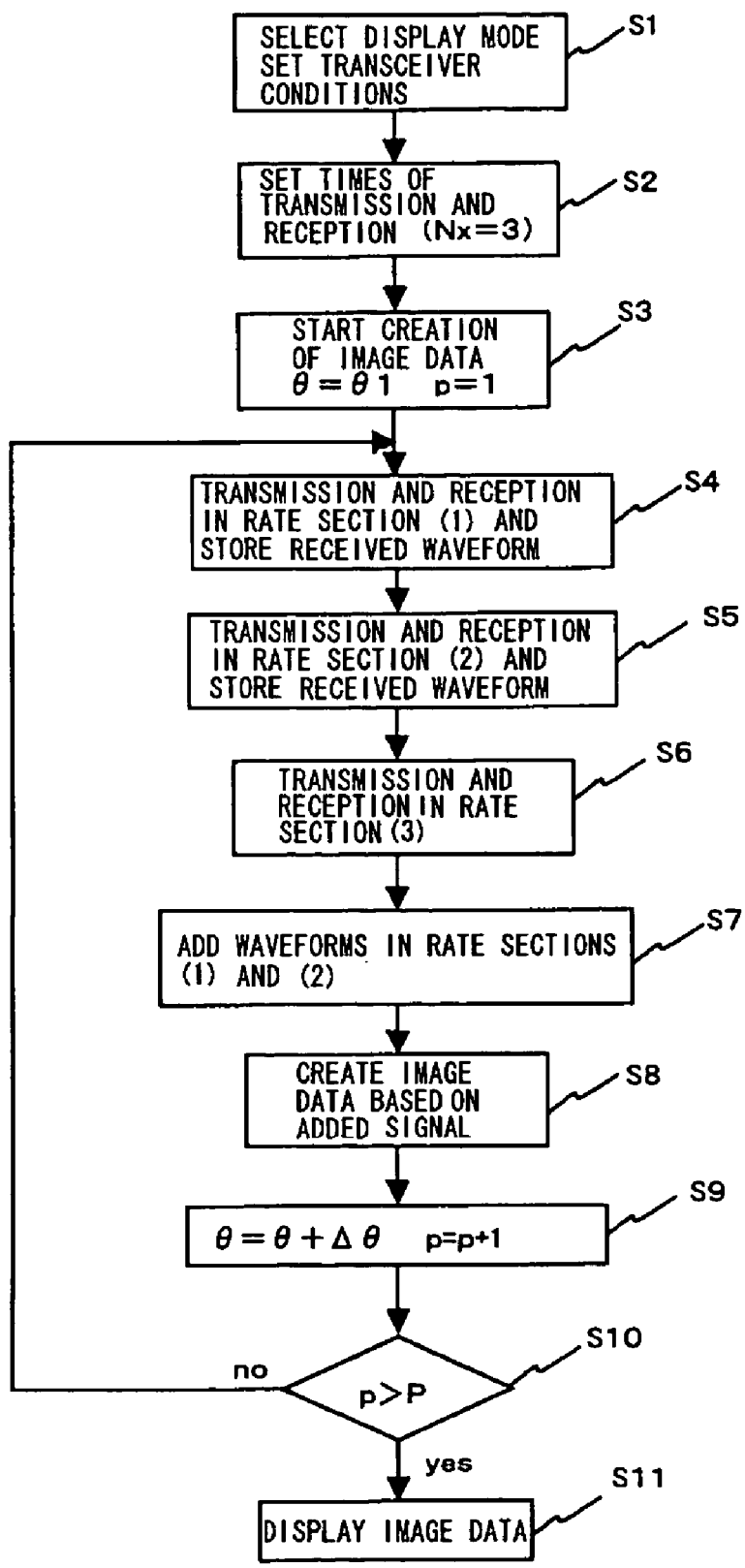
FIG. 3 is a flow chart for creating image data in the first embodiment.

A method for creating the image data will be explained in reference to FIG. 2 through FIG. 8. FIG. 3 is a flow chart of a process for creating the image data. The operator select the THI mode which is an image display mode of the first embodiment, and sets an imaging range (sector angle and depth) and the transceiver conditions, such as the rate cycle (Step S1). The memory circuit of the system control part 6 stores in advance a maximum receiving time Th of the received signal corresponding to probe ID, and reads the maximum receiving time Th and the rate cycle Tr according to the probe ID supplied from the ultrasonic probe 1. The CPU of the system control part 6 calculates a transmission and reception time Nx based on the following equation (1).

$$Nx=[Th/Tr]+1 \qquad \text{equation (1)}$$

"[Th/Tr]" in the equation (1) means rounding up such that the number Nx is integer. For instance, when $1<T_h/T_r<2$, Nx=3. The following explanation is a case of Nx=3.

Figure 4:
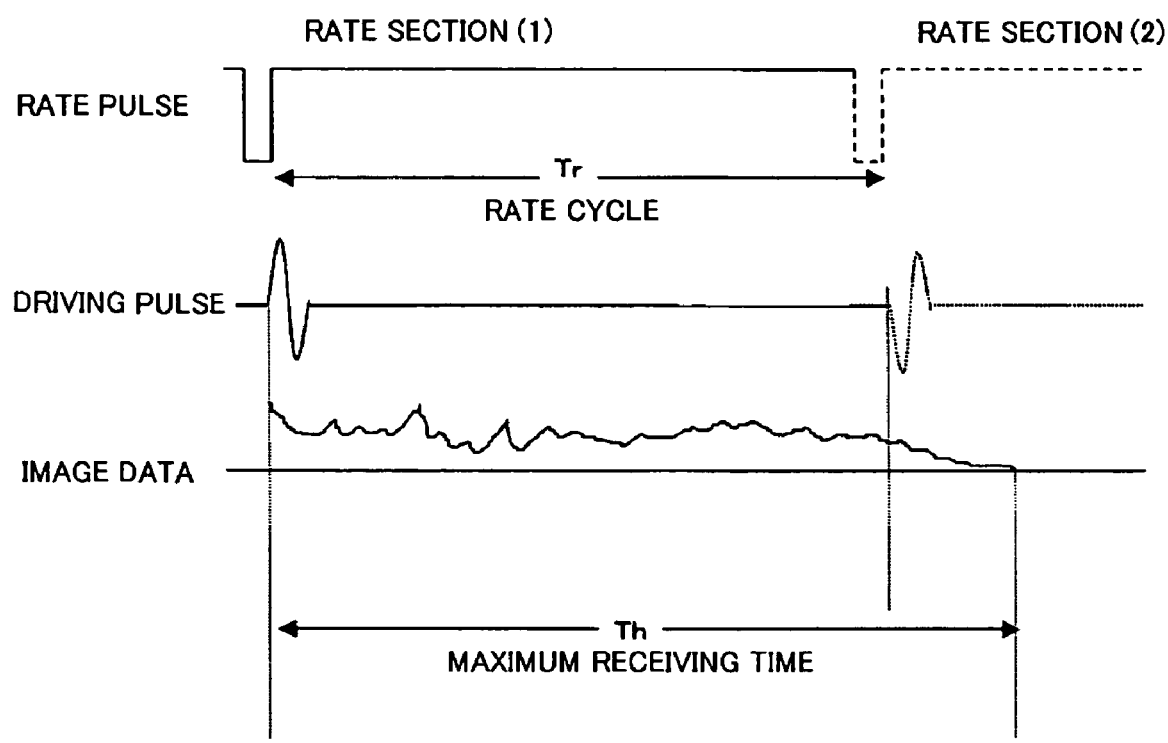
FIG. 4 is an illustration for explaining a remaining echo in the first embodiment.

FIG. 4 shows relationship between the maximum receiving time Th and the rate cycle Tr. In FIG. 4, the rate pulse that is repeatedly output from the rate pulse generator 11 at the rate cycle Tr, the driving pulse that is output from the pulsar 13 based on the rate pulse, and the image data obtained by driving the vibration element based on the driving pulse are shown, respectively. When a reflection from a deep portion or multiple reflections exists and the maximum receiving time Th is longer than the rate cycle Tr, the remaining pulse generated by the first driving pulse is received in the second rate section when the second transmission and reception is performed.

After the setting of the number of times Nx of ultrasonic transmission and reception is completed, the system control part 6 reads the information about the ultrasonic frequency and the frequency band of the ultrasonic probe 1 stored in the memory circuit of the system control part 6 based on the probe ID, and sets up the filter characteristic of the filter circuit 19, such as the center frequency, the frequency band and amount of attenuation in cut off frequency. For example, when resonance frequency of the vibration element of the ultrasonic probe 1 is fo, the center frequency of the filter circuit 19 is set as 2fo. When the THI mode is not used, the harmonic extraction part 4 may passed by an electric switch. When the setting of THI is completed, the start command inputted by the operator with the input part 7 is send to the system control part 6 and the harmonic image data is created (Step S3).

When the transmission of the ultrasonic wave is performed, the rate pulse generator 11 supplies to the transmission delay circuit 12 the rate pulse that determines the rate cycle Tr of the ultrasonic pulse irradiated to the patient based on the control signal from the system control part 6. The transmission delay circuit 12 gives the delay time for focusing the ultrasonic wave on the predetermined depth and gives the delay time for irradiating the ultrasonic wave in the first scanning direction θ1 to the rate pulse of the 1st rate section. The rate pulse is supplied to the pulsar 13a. Based on the positive polarized driving pulse, the pulsar 13a drives the vibration element of the ultrasonic probe 1 to irradiate the ultrasonic pulse of the center frequency fo to the patient (Step S4). The transmission delay circuit 12 and the pulsar 13 include M channels, and each channel is independently connected to each ultrasonic vibration element of the ultrasonic probe 1 via multi cable lines 26.

A part of the ultrasonic wave irradiated to the patient is reflected on border face of the internal organs where sound impedance is different, or on the tissue. In this case, the reflective ultrasonic wave of the center frequency 2fo is newly generated by the non linear characteristic of the patient tissue. That is, the reflected ultrasonic wave reflected on the tissue of the patient includes signal at the same center frequency fo as the transmitted frequency (basic component) and signal at the center frequency 2fo (harmonics component).

Figure 5:
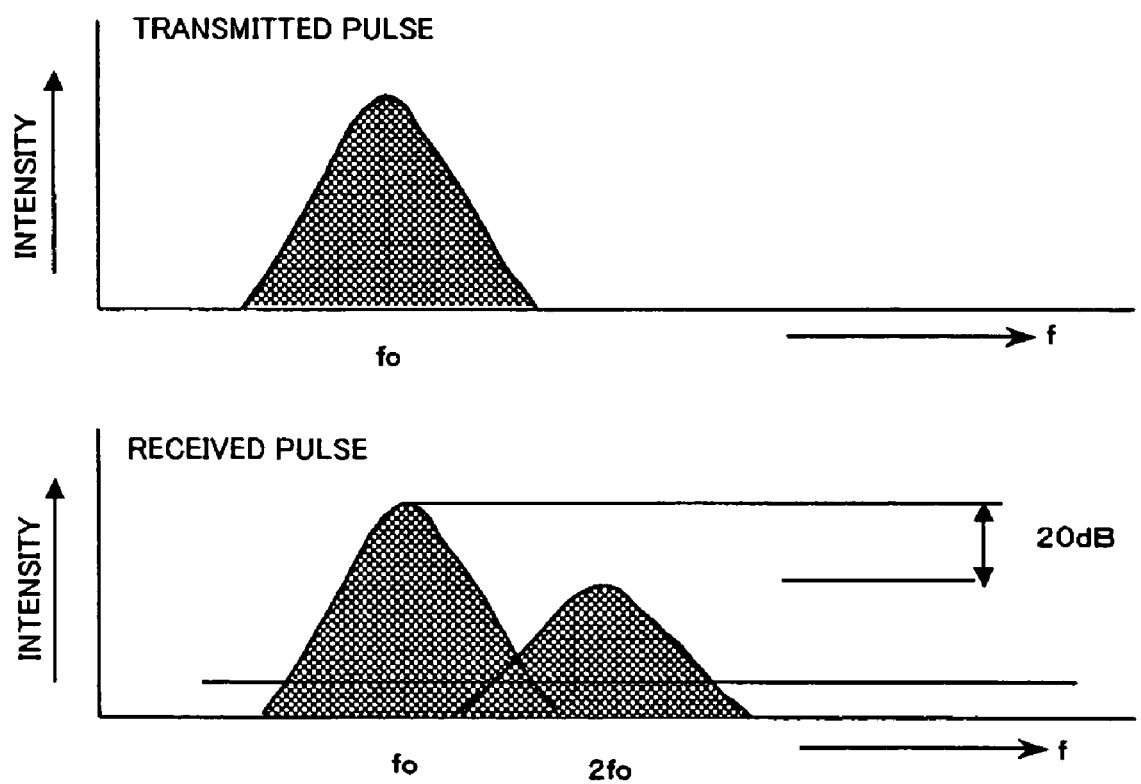
FIG. 5 is a graph of a harmonic component of an ultrasonic wave.

FIG. 5 shows frequency spectrums of the transmitted ultrasonic signal and the received ultrasonic signal. The transmitted ultrasonic signal has the spectrum of the center frequency fo. On the other hand, the received ultrasonic signal has the basic component of the center frequency fo and the harmonic component of the center frequency 2fo. Generally the harmonics component is smaller the basic component by about 20 dB.

When the ultrasonic pulse having a wide frequency spectrum is transmitted in order to obtain a high resolution image, the basic component and harmonic component also have the wide frequency spectrum. For this reason, a high pass portion of the basic component and a low pass portion of the harmonic component are not separated in many cases. In the first embodiment, the received signal in the 1st rate section may not be stored as the image data, since a purpose of transmission of the 1st ultrasonic wave is to obtain the remaining echo in the 2nd rate section.

The system control part 6 sends the control signal to the transmitter 2 to switch the pulsar from the pulsar 13a to the pulsar 13b. The ultrasonic wave generated by the negative polarized driving pulse is transmitted to the first scanning direction θ1. That is, the rate pulse generator 11 supplies the rate pulse of the 2nd rate section to the transmission delay circuit 12, and the transmission delay circuit 12 gives the same delay time for beam focusing as that of the 1st rate section. The delay time for determining the direction of the transmitted ultrasonic wave in the 1st direction θ1 is also imposed on the rate pulse that is supplies to the pulsar 13b.

The pulsar 13b drives the ultrasonic vibration element of the ultrasonic probe 1 by the driving pulse of negative polarity, and the ultrasonic pulse is irradiated to the patient. A part of irradiated ultrasonic wave is reflected on the face of the internal organs where sound impedance is different, or on the tissue. The reflected ultrasonic wave is received by the same ultrasonic probe as that for transmitting, and converted to the electric signal. The electric signal is amplified by the preamplifier 14 and is A/D converted by the A/D converter 15. After the predetermined delay time is imposed on the digital signal by the beam former 16 based on the control signal from the system control part 6, an additional process is performed in the adder 25. At this time, in the beam former 16, the delay time for focusing the ultrasonic wave on the predetermined depth and the delay time for irradiating the ultrasonic wave in the first scanning direction θ1 are set based on the control signal from the system control part 6. The received signal received within the 2nd rate section is stored in the waveform memory 17 of the harmonic extraction part 4 (Step S5). The stored received signal includes the remaining echo by the 1st driving pulse. The system control part 6 switches again the pulsar 13b to the pulsar 13a, and the ultrasonic wave is transmitted to and received from the same direction (θ1). That is, the rate pulse generator 11 supplies the rate pulse of the 3rd rate section to the transmission delay circuit 12, and the transmission delay circuit 12 gives the same delay time for focusing and for determining direction as that of the rate pulse of the 1st rate section and the 2nd rate section to the pulsar 13a. The pulsar 13a drives the vibration element of the ultrasonic probe 1 by the positive polarized driving pulse to transmit the ultrasonic wave to the patient. The reflective wave from the patient is converted to the received signal by the ultrasonic probe 1, and added by the adder 25 via the preamplifier 14, A/D converter 15 and the beam former 16 (Step S6).

Among the added signals, the received signal received within the 3rd rate section is sent to the adder 18 of the harmonic extraction part 4. At this time, the stored received by signal received the 3rd rate section includes the remaining echo by the 2nd driving pulse. The system control part 6 reads the received signal generated by the 2nd driving pulse, the read received signal and the received signal generated by the 3rd driving pulse in the adder 18 (Step S7).

Thus, the received signal acquired by the negative polarized driving pulse and the received signal acquired by the positive polarized driving pulse are added in the adder 18, and the output is sent to the filter circuit 19. The output of the filter circuit 19 is sent to the signal processing part 5 and is processed by the envelope detector 20 and the logarithmic converter 21 to create the image data (Step S8). The image data is temporarily stored in the display memory 22.

The above-mentioned process is repeated by Δθ. That is, the process is performed to the direction θp=θ1+(p−1)Δθ, where p=2 through P. The system control part 6 creates the image data, changing the transmission and reception direction based on the delay time of the transmission delay circuit 12 and the beam former 16 (Step S4 through S10). Thus, the sector scan from the 1st direction θ1 through Pth direction θp, and when the image data for a single image is stored, the system control part 6 reads out the image data stored in the display memory 22 to display the image data on the CRT monitor 24 via the converter 23 (Step S11).

Figure 6A:
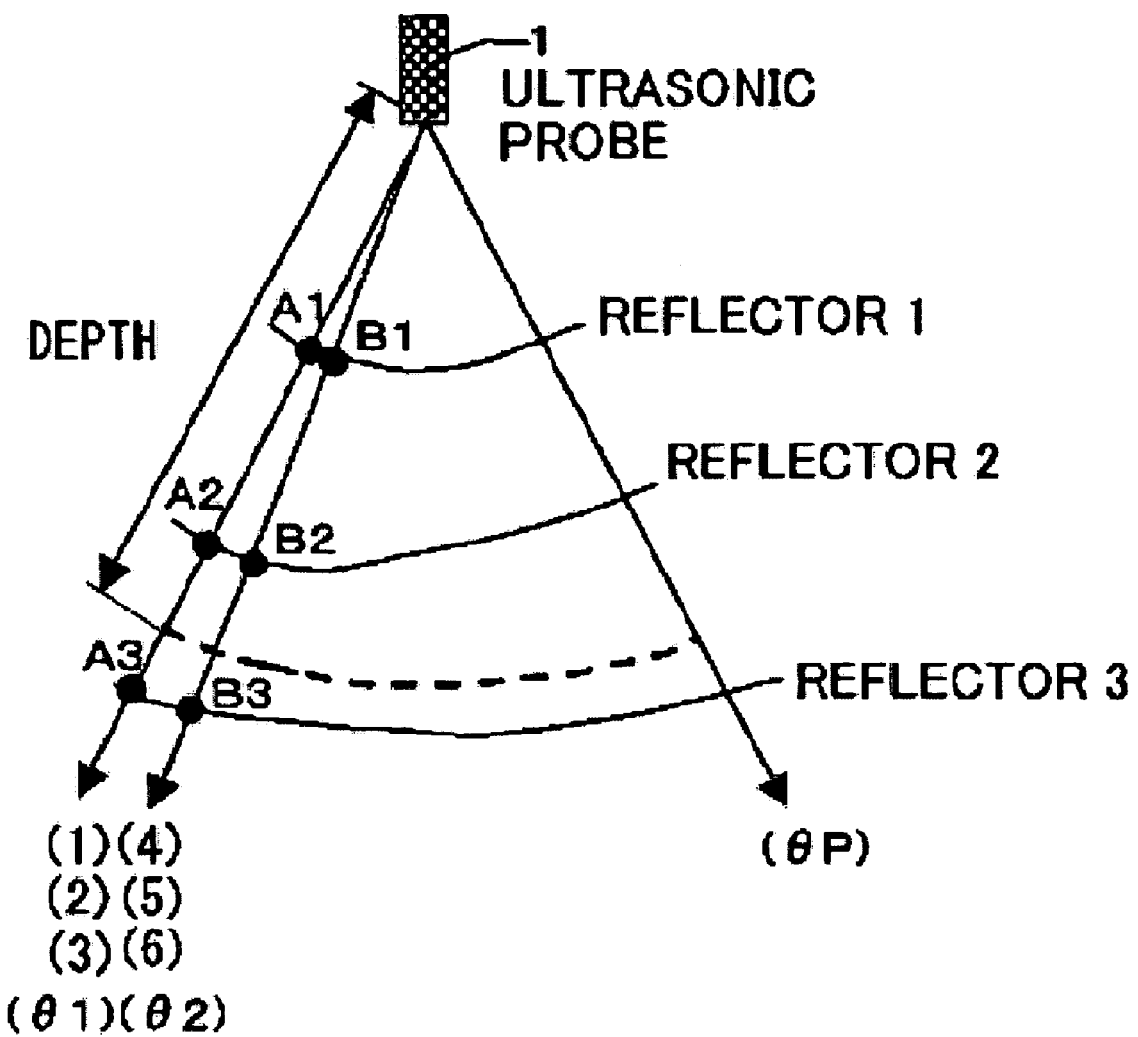
FIG. 6A and FIG. 6B are illustrations for explaining the remaining echo in the first embodiment.
Figure 6B:
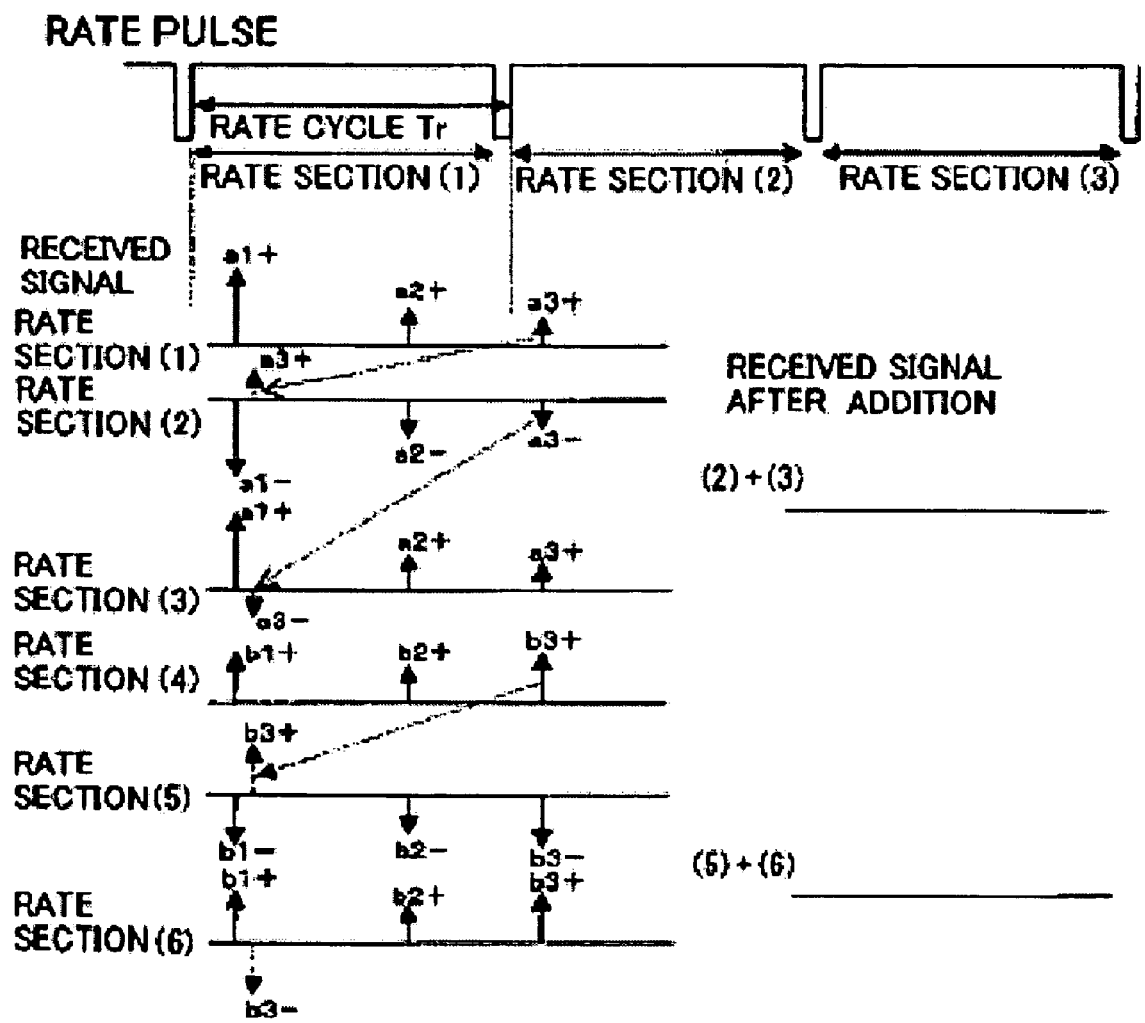

Reduction of the remaining basic component will be explained in reference to FIG. 6A and FIG. 6B. The transmission and reception is performed in the rate sections (1) though (3) to the 1st direction θ1, and subsequently the transmission and reception is performed in the rate sections (4) though (6) to the 2nd direction θ2(θ2=θ1+Δθ) that is adjacent to the 1st direction θ1. The reflectors 1 through 3 are positioned along the transmission and reception direction. It takes longer to perform the ultrasonic transmission and reception to the reflector 3 than the rate cycle Tr. FIG. 6B shows a rate pulse for determining the irradiation timing of the ultrasonic wave, and the received signals from the reflector 1, 2 and 3 within the rate section (1) through (6). Size and polarity of the basic component are indicated by arrows. The reflected signal based on the positive polarized driving pulse is indicated as "+" mark, and the negative polarized driving pulse is indicated as "−" mark. Further, FIG. 6B shows the result of addition of the basic components obtained in the rate section 2 and the rate section 3. Also, FIG. 6B shows the result of addition of the basic components obtained in the rate section 5 and the rate section 6. In this case, the 1st, 3rd, 4th and 6th driving pulses are sent from the pulsar 13a and are driven by the positive polarized driving pulse. The 2nd and 5th driving pulses are sent from the pulsar 13b and are driven by the negative polarized driving pulse. That is, the ultrasonic pulse irradiated in the 1st scanning direction θ1 by the positive polarized driving pulse is reflected in the reflector A1 through A3, and the positive polarized basic components of a1+, a2+ and a3+, respectively are received.

Subsequently, the reflected ultrasonic pulse transmitted by the negative polarized driving pulse to the same direction θ1 makes the negative polarized basic components of a1−, a2− and a3. Since the ultrasonic pulse by the 2nd driving pulse is irradiated before receiving the reflected signal of a3+ from the reflector A3 by the 1st driving pulse, the received signal a3+ from the reflector A3 includes the reflected signal of a3+ is mixed to the reflected signal of a1−. That is, in the 2nd rate section (2), the received signals a1− and a2− which are reflected on the reflectors A1 and A2 are obtained, and the received signal a3+ that reflected on the reflector A3 is received as well.

Furthermore, to the same scanning direction θ1, the ultrasonic pulse irradiated by the 3rd positive polarized driving pulse is reflected in the reflector A1 through A3 as well as the 1st driving pulse, and the basic components which have the positive polarized intensity of a1+, a2+ and a3+ are obtained as the received signals. In the 3rd rate section, the received signal a3− from the reflector A3 is mixed with the received signals of a1+ and a2+ that are reflected on the reflectors A1 and A2.

Since the basic components a1−, a2− and a3+ received within the 2nd rate section (2) and the basic components a1+, a2+ and a3− received within the 3rd rate section (3), are the same or similar size and are reverse polarity, each basic component can be reduced. Similarly, regarding to the 2nd direction θ2, the same process is performed using the received signals received within the rate sections (4) through (6). That is, the received signal which has the basic components of b1+, b2+ and b3+ is acquired by the 4th positive polarized driving pulse. The ultrasonic pulse irradiated by the 5th negative polarized driving pulse to the same scanning direction θ2 is reflected in the reflector B1, B2 and B3. The received signal which has the basic components of b1−, b2− and b3− are received. Since the ultrasonic pulse by the 5th driving pulse is irradiated before receiving the reflected signal from the reflector A3 by the 4th driving pulse, the positive polarized reflected signal of b3+ is mixed to the reflected signal of b1− and b2−. Furthermore, in the direction θ2, the positive polarized basic component is obtained from the reflector B1 through B3 by the reflected intensity b1+, b2+ and b3+. In the 6th rate section, the negative polarized reflected signal of b3− is mixed to the reflected signal of b1+ and b2+. Therefore, by adding the received signal obtained within the 5th rate section to the received signal obtained within the 6th rate section, the basic component is reduced.

Figure 7:
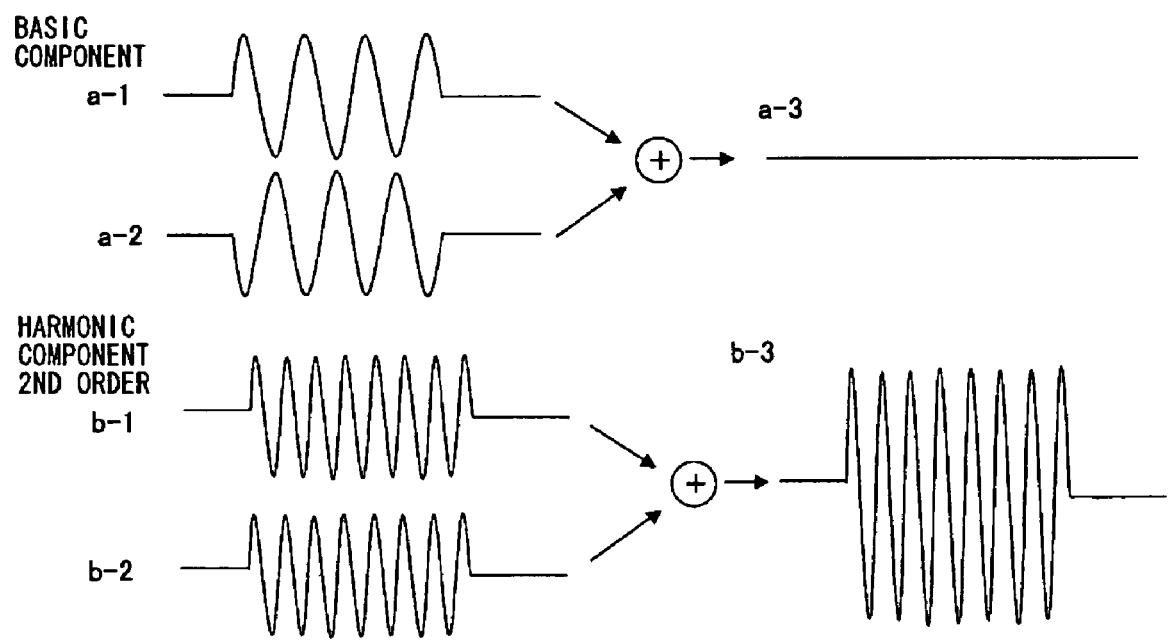
FIG. 7 is an illustration for explaining polarity of a basic component and the harmonic component in a pulse subtraction.

Although the above explanation is related to the basic component, the harmonic component is not reversed even if the transmitted signal is reversed. FIG. 7 is shows the result of addition of the basic components and the result of addition of the harmonic components. As described above, the basic component is reduced as shown a−3 since the basic components (a−1 and a−2) are reversed according to the polarity of the transmitted signal. On the other hand, since the harmonic components (b−1 and b−2) are not reversed according to the polarity of the transmitted signal, the harmonic component b−3 is doubled.

In the meantime, in order to reduce influence of the remaining echo, the rate section is conventionally set long. When the conventional method is applied to the pulse subtraction, the motion artifact easily appears.

Figure 8:
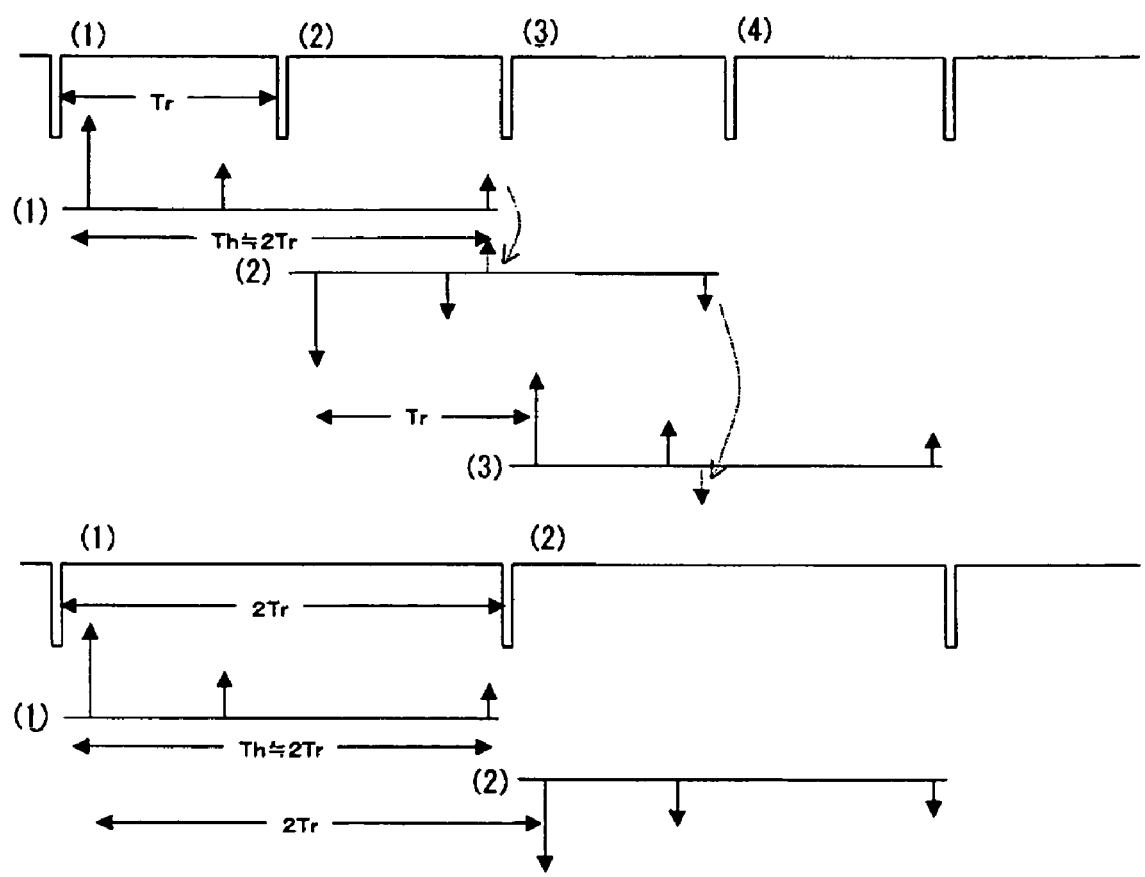
FIG. 8 is an illustration for explaining reduction of a motion artifact in the first embodiment.

The effect of the first embodiment to this problem will be explained in reference to FIG. 8. The remaining echo using the conventional method is shown in the bottom portion of FIG. 8, and the remaining echo using the method of the first embodiment is shown in the top portion of FIG. 8. In the conventional method, the maximum receiving time ($T_h$) is approximately equal to the two-fold rate cycle (2Tr). In the method of the first embodiment, the difference of the received signals that are added, such as the signals by the 2nd and 3rd driving pulses is the rate cycle Tr. Therefore, since the rate cycle of the first embodiment is shorter than that of the conventional method, it can appropriately extract the harmonic component without increase of the motion artifact. Moreover, since the filtering method is used together with the shorter rate cycle in the first embodiment, the remaining basic component which remains as the motion artifact can be reduced further.

Modification of the First Embodiment

A modification of the first embodiment will be explained below. When a large reflector exists in a deep portion of the patient or serious multi-reflection occurs, it is desirable to enlarge the maximum receiving time in order to reduce the remaining echo. However, the large Th increases transmission and reception time N in the same direction, and rame frequency rate decreases. Since the relationship between the remaining echo and the frame frequency is a trade-off, it is desirable for the operator to set an appropriate Nx. In the modification, the transmission and reception time Nx is set based on the following equation (2).

$$Nx=[Th \times K/Tr]+1 \quad (0<K \leq 1) \qquad \text{equation (2)}$$

"[Th×K/Tr]" in equation (2) means rounding up such that the number Nx is integer as well as equation (1). Th indicates the maximum receiving time from a time when the vibration element is driven to a time when the reflective ultrasonic wave mostly disappears. K indicates a weighted coefficient that the operator inputs by the input part 7. When the real time characteristic is given more importance than the reduction of the remaining echo, such as occurs in ultrasonic diagnosis in an angiography, the operator sets a relatively small K. In the modification, it is easy to appropriately adjust the rame frequency and the remaining echo, using THI by the pulse subtraction.

Second Embodiment

A second embodiment will be explained below. In the second embodiment, after reversing the polarity of the driving pulse and the transmission and reception in a predetermined direction are performed 2 times, the transmission is stopped and only the reception is performed to receive the reflective ultrasonic wave from the deep portion or the multi reflective ultrasonic wave. By adding the all received signals, the remaining echo is reduced.

Since the composition of the apparatus in the second embodiment is similar to the like as that of the first embodiment shown in FIG. 2, the detailed explanation is omitted. A process for creating image data will be explained in reference to FIG. 9 and FIG. 10.

Figure 9:
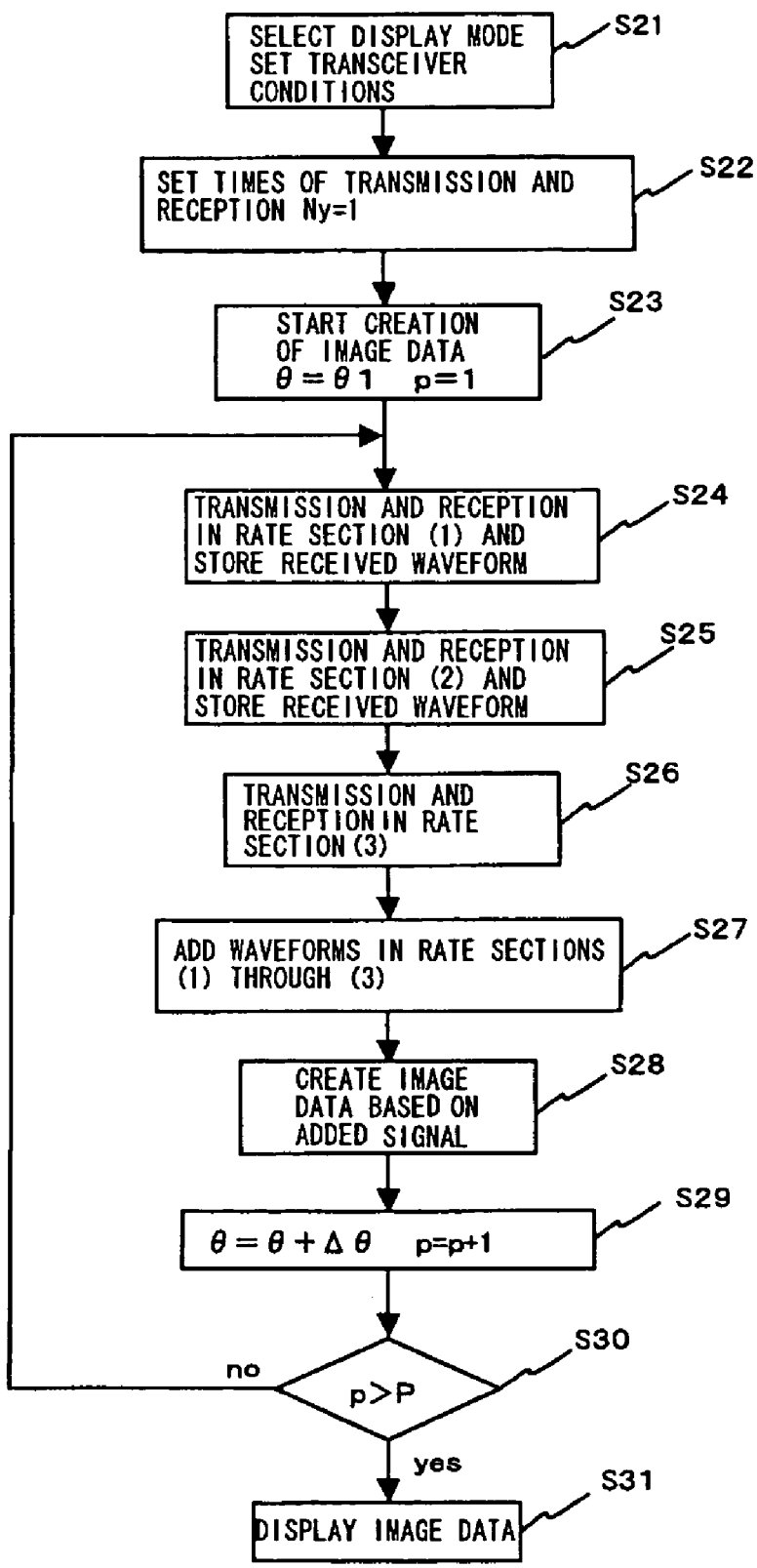
FIG. 9 is a flow chart for creating image data in the second embodiment.

FIG. 9 is a flow chart which shows the creation procedure of image data. An operator selects THI mode by the input part 7, and sets up the transceiver conditions (Step S21). The system control part 6 receives the selection signal of the image display mode and transceiver conditions from the input part 7, and reads probe ID information from the ultrasonic probe 1. The maximum receiving time Th is stored in advance in the memory circuit of the system control part 6 corresponding to each probe ID. The system control part 6 reads the maximum receiving time Th corresponding to the probe ID sent from the ultrasonic probe 1 and the rate cycle Tr determined based on the transceiver conditions. The number of only reception times Ny in addition to transmission and reception times Nx is set based on the following equation (3) (Step S22).

$$Ny = [Th/Tr] - 1 \quad \text{equation (3)}$$

"[Th/Tr]" in the equation (3) means rounding up such that the number Ny is an integer. For instance, when $1 < Th/Tr \leq 2$, Ny=1. The following explanation is a case of Ny=1. When the set of the Ny is completed, the system control part 6 reads the information about the ultrasonic frequency and the frequency band of the ultrasonic probe 1 stored in the memory circuit based on this probe ID information, and sets up the filter characteristic, such as the center frequency in the filter circuit 19 of the harmonic extraction part 4, a bandwidth, and amount of attenuation in the cut off frequency range based on the information. When the setup in the THI mode is completed, the operator inputs the imaging start command by the input part 7 and the command is sent to the system control part 6. The transmission and reception of the ultrasonic wave is started based on the command (Step S23).

When the ultrasonic wave is transmitted, the rate pulse generator 11 supplies the rate pulse to the transmission delay circuit 12 according to the control signal from the system control part 6. The transmission delay circuit 12 gives the delay time for focusing the transmitted ultrasonic wave and the delay time for determining the direction of the rate pulse of the 1st rate section, and supplies the rate pulse to the pulsar 13a. The pulsar 13a drives the ultrasonic vibration element of the ultrasonic probe 1 by the positive polarized driving pulse, and the ultrasonic pulse is irradiated to the patient. The reflected ultrasonic wave is received by the same ultrasonic vibration element and is changed into an electric received signal. After the received signal is amplified to a predetermined size by the preamplifier 14 of the receiver 3, the amplified received signal is changed into a digital signal by the A/D converter 15. Further, the digital signal is given a predetermined delay time by the beam former 16 based on the control signal from the system control part 6, and the signal is added in the adder 25. The received signal received in the 1st rate section among the received signals added by the adder 25 is stored in the waveform memory 17 of the harmonic extraction part 4 (Step S24).

The system control part 6 sends a control signal to the transmitter 2 to switch the pulsar 13 from the pulsar 13a to the pulsar 13b, and the ultrasonic wave is transmitted to and received in the same scanning direction θ1. That is, the rate pulse generator 11 supplies the rate pulse of the 2nd rate section to the transmission delay circuit 12, and the transmission delay circuit 12 gives the same delay time for focusing as that of the rate pulse of the 1st rate section, and the delay time for determining the scanning direction of the ultrasonic wave in the scanning direction θ1 to the rate pulse of the 2nd rate section, and supplies this rate pulse to pulsar 13b. The pulsar 13b drives the ultrasonic vibration element by the negative polarized driving pulse to irradiate the ultrasonic pulse to the patient. A part of the irradiated ultrasonic wave is reflected by the border of internal organs and a part is reflected by the patient tissue in which sound impedance is different. The reflected wave from the patient is converted to the received signal by the ultrasonic probe 1, and added by the adder 25 via the preamplifier 14, A/D converter 15 and the beam former 16. The received signal received in the 2nd rate section among the received signals added in the adder 25 is stored in the waveform memory 17. The received signal stored includes the remaining echo by the 1st driving pulse as shown in FIG. 4 (Step S25).

Subsequently, the system control part 6 stops the drive of the pulsar 13 in the 3rd rate section, and performs only reception of the ultrasonic wave from the same scanning direction θ1. At this time, the ultrasonic reflective wave from the patient is the remaining echo by the 2nd driving pulse, and the reflective ultrasonic wave is converted to the received signal by the ultrasonic probe 1, and added by the adder 25 via the preamplifier 14, A/D converter 15 and the beam former 16 (Step S26).

The received signal received in the 3rd rate section among the received signals added in the adder 25 is stored in the waveform memory 17, and is sent to the adder 18. The adder 18 reads the received signals of the 1st rate section and the received signal of the 2nd rate section from the waveform memory 17, and adds the read signals to the received signal of the 3rd rate section. (Step S27). The output of the adder 18 is sent to the filter circuit 19 of the harmonic extraction part 4 to reduce the motion artifact that is not removed by the pulse subtraction. The output of the filter circuit 19 is sent to the signal processing part 5 and is processed by the envelope detector 20 and the logarithmic converter 21 to create the image data. The image data is temporarily stored in the display memory 22 (Step S28). The above-mentioned process is repeated by Δθ. That is, the process is performed to the direction θp=θ1+(p−1) Δθ, where p=2 through P. The system control part 6 creates the image data, changing the transmission and reception direction based on the delay time of the transmission delay circuit 12 and the beam former 16 (Step S24 through S30). When the image data for a single image is stored, the system control part 6 reads out the image data stored in the display memory 22 to display the image data on the CRT monitor 24 via the converter 23 (Step S31).

Figure 10A:
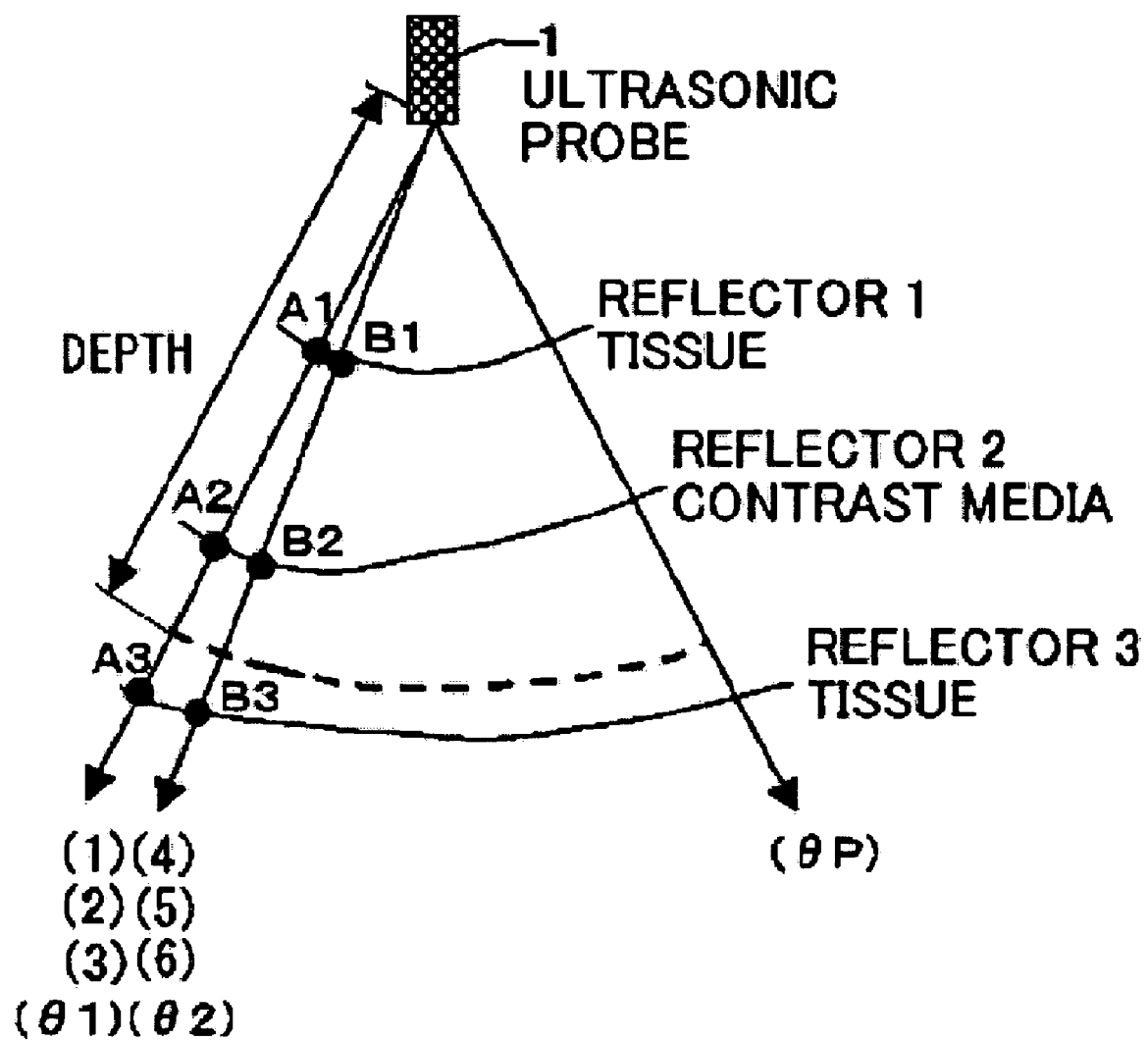
FIG. 10A and FIG. 10B are illustrations for explaining a remaining echo in the second embodiment.
Figure 10B:
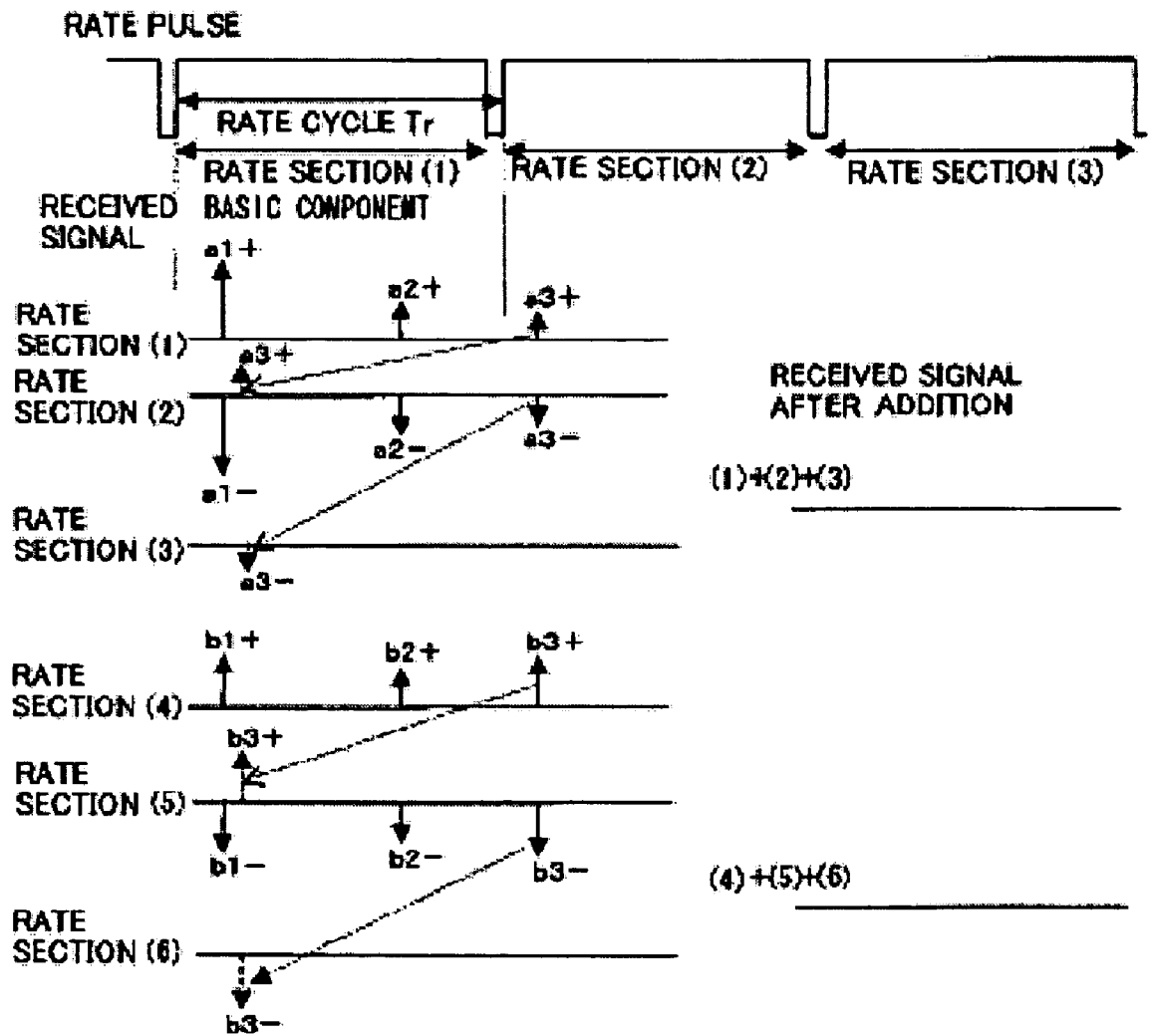

Reduction of the remaining basic component will be explained in reference to FIG. 10A and FIG. 10B. The transmission and reception is performed in the rate sections (1) though (3) to the 1st direction θ1, and subsequently the transmission and reception is performed in the rate sections (4) though (6) to the 2nd direction θ2 that is adjacent to the 1st direction θ1. The reflectors 1 through 3 are positioned along the transmission and reception direction. It takes longer to perform the ultrasonic transmission and reception to the reflector 3 than the rate cycle Tr. FIG. 10B shows the rate pulse for determining the irradiation timing of the ultrasonic wave, and the received signals from the reflector 1, 2 and 3 within the rate section (1) through (6). Size and polarity of the basic component are indicated as arrow. Further, FIG. 10B shows the result of addition of the basic components obtained in the rate section 1 through the rate section 3. Also, FIG. 10B shows the result of addition of the basic components obtained in the rate section 4 through the rate section 6. In this case, the vibration elements are driven by the positive polarized 1st and 4th driving pulses by the pulsar 13a in the 1st and 4th rate sections. The vibration elements are driven by the positive polarized 2nd and 5th driving pulses by the pulsar 13b in the 2nd and 5th rate sections. In the 3rd and 6th sections, the transmission of the ultrasonic wave is stopped, and only reception of the remaining echo by the 2nd and 5th driving pluses continues. That is, the ultrasonic pulse irradiated in the 1st scanning direction θ1 by the positive polarized driving pulse is reflected in the reflectors A1 through A3, and the positive polarized basic components of a1+, a2+ and a3+ are respectively received.

Subsequently, the reflective ultrasonic pulse transmitted by the negative polarized driving pulse to the same direction θ1 makes the negative polarized basic components of a1−, a2− and a3−. Since the ultrasonic pulse by the 2nd driving pulse is irradiated before receiving the reflected signal from the reflector A3 by the 1st driving pulse, the received signal from the reflector A3 is mixed with the reflected signal in the rate section (2). That is, in the 2nd rate section (2), the received signals a1− and a2− that are reflected on the reflectors A1 and A2 are obtained, and the received signal a3+ that is reflected on the reflector A3 is received as well. In the 3rd section, the transmission of the ultrasonic wave is stopped, the only reception continues. The received signal receive in the 3rd section is the remaining echo that is not received in the 2nd section. The received signals received in the 1st section, the 2nd section and the 3rd section, are added by the adder 18 in order to reduce the basic component in the received signal. Regarding to the 2nd scanning direction θ2, the basic component can be reduced by using the received signals received in the 4th rate section (4) through the 6th rate section.

In the second embodiment, since the time interval between the received signals that are added can be shortened, the remaining echo can be reduced without increase of the motion artifact. Further, since the ultrasonic pulse is transmitted only two times, energy of the ultrasonic wave can be reduced. For instance, the energy is reduced to 2/Nx in comparison with the first embodiment. Moreover, since the filtering method is further used, the remaining basic component which remains as the motion artifact can be reduced further. The modification of the first embodiment may be applied to the second embodiment. Moreover, although the harmonic component is extracted in the second embodiment, the basic component may be extracted by subtracting the received signals over the continued rate sections.

Third Embodiment

A third embodiment will be explained below. In the third embodiment, two transmissions and receptions are performed in the same direction in the 1st rate section and the 2nd rate section, using two driving pulses of the same polarity. After the two transmissions and receptions, only ultrasonic reception of Ny times is performed, and subsequently, the remaining echo that skips over the rate section is received from the same direction. By adding and subtracting the received signals in the rate sections of Ny+2, the received signal reflected on the tissue is reduced and the received signal reflected on the contrast media is extracted to create the image data. Hereinafter, in order to simplify explanation, the received signal reflected on the tissue is referred to as tissue signal, and the received signal reflected on the contrast media is referred to as contrast media signal.

(Composition of Apparatus)

Figure 11:
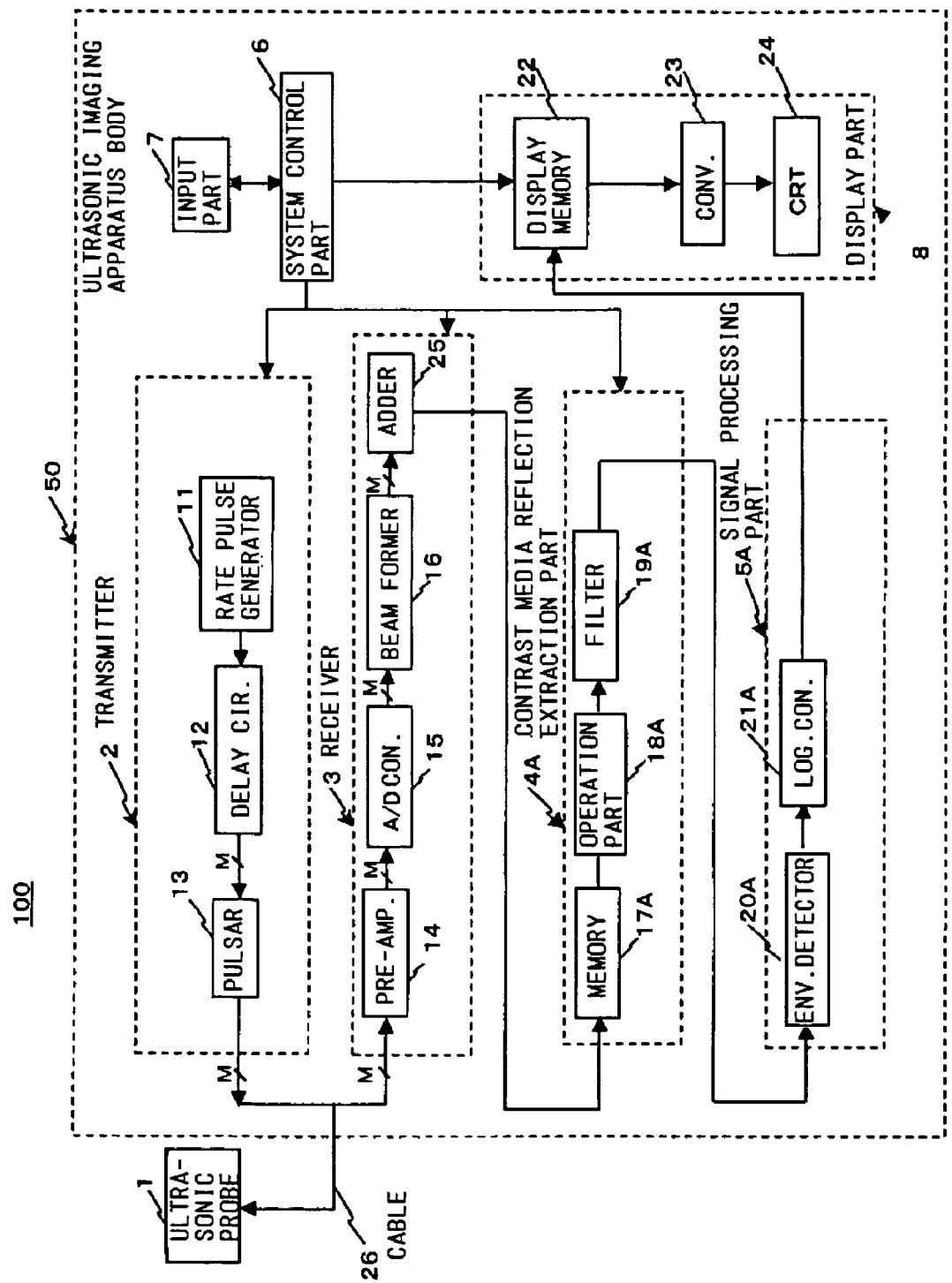
FIG. 11 is a block diagram of an ultrasonic imaging apparatus of a third embodiment.

FIG. 11 is a block diagram of an ultrasonic imaging apparatus 100. In the third embodiment, a contrast media reflection extraction part 4A is provided instead of the harmonic extraction part 4 of the first embodiment. The contrast media reflection extraction part 4A includes a waveform memory 17A, an operation part 18A and a filter circuit 19A. The waveform memory 17A stores the received signal acquired by two ultrasonic transmissions to and receptions from a predetermined direction, and the received signals acquired by the ultrasonic reception of Ny times. The operation part 18A performs addition and subtraction processing to the received signals acquired to the predetermined direction, and reduces the tissue signal. The filter circuit 19A is a filter circuit for performing separation of a basic component and a harmonic component contained in the contrast media signal. As disclosed in Japanese Patent Publication (Kokai) No. 8-336527, when the ultrasonic wave of the center frequency fo is irradiated to the patient tissue or the contrast media, the harmonics component (2fo) is newly generated according to a non linear characteristic. The harmonic component is received together with the basic component (fo). The filter circuit 19A may be provided prior to the waveform memory 17A. In this case, the basic component or the harmonic component is selected by the filter circuit 19, and the selected component is stored in the waveform memory 17A. The operation part 18A extracts the contrast media signal by adding and subtracting the received signals stored.

The system control part 6 controls the whole apparatus and each part thereof, such as the transmitter 2, the receiver 3, the contrast media reflection extraction part 4A, and the display part 8, based on the instruction signal from the input part 7. The system control part 6 includes the memory circuit and CPU, and the memory circuit stores the patient information sent from the input part 7, the transceiver conditions and the image display mode. The memory circuit further stores the maximum receiving time Th corresponding to ID of the ultrasonic probe 1. The CPU of the system control part 6 sets up the filter characteristic in the filter circuit 19A of contrast media reflection extraction part 4A, such as the center frequency and the frequency band, based on the probe ID supplied from the ultrasonic probe 1 and the image display mode information inputted by the input part 7. The CPU of the system control part 6 reads the rate cycle Tr set by the input part 7 and by the maximum receiving time Th corresponding to the mentioned probe ID, calculates the number of times Ny of the ultrasonic reception performed in the same direction. Based on the calculation result, the addition and subtraction processing in operation part 18A of the contrast media reflection extraction part 4A is controlled.

(Creation of Image Data)

Figure 12:
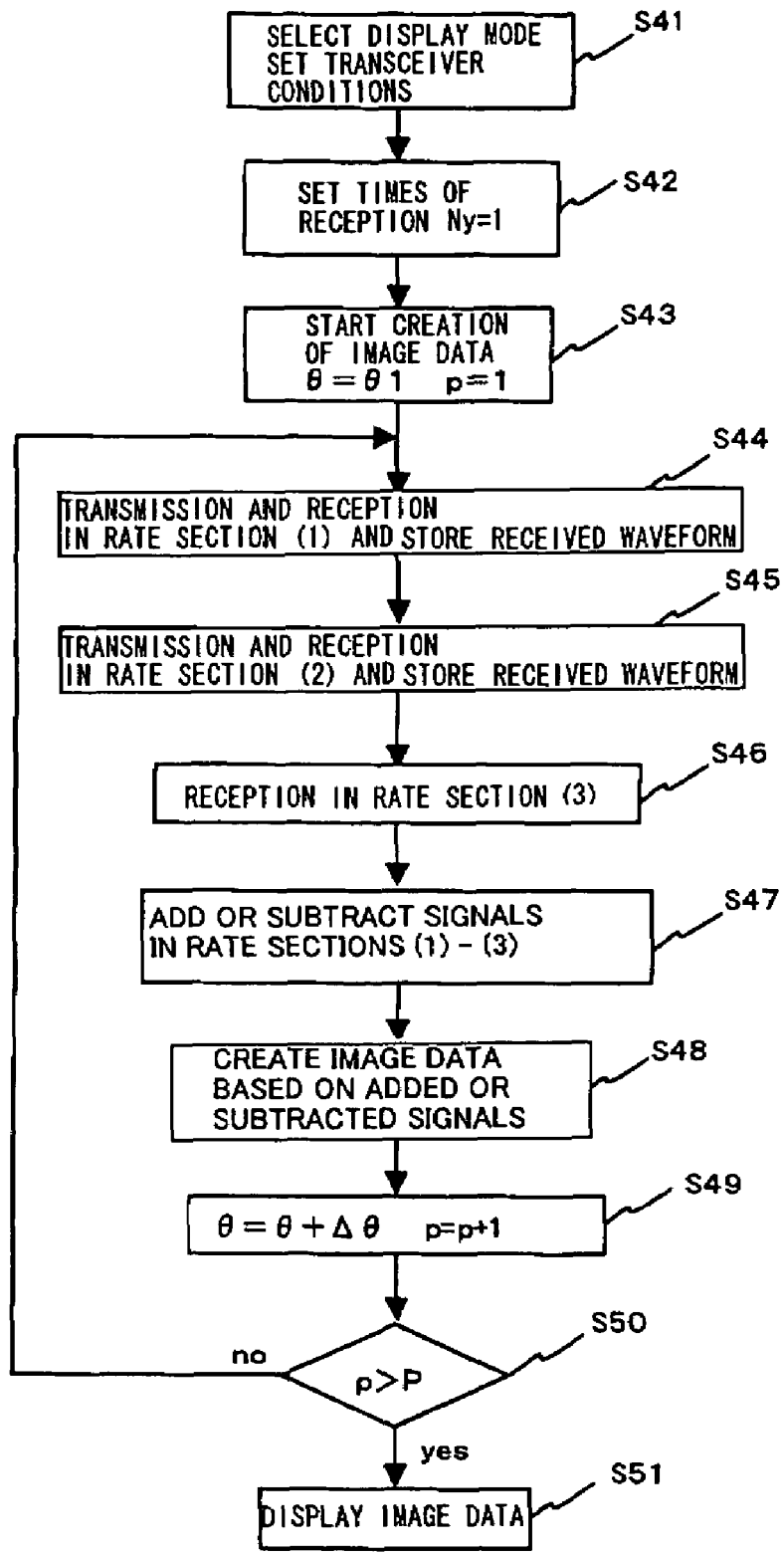
FIG. 12 is a flow chart for creating image data in the third embodiment.
Figure 13A:
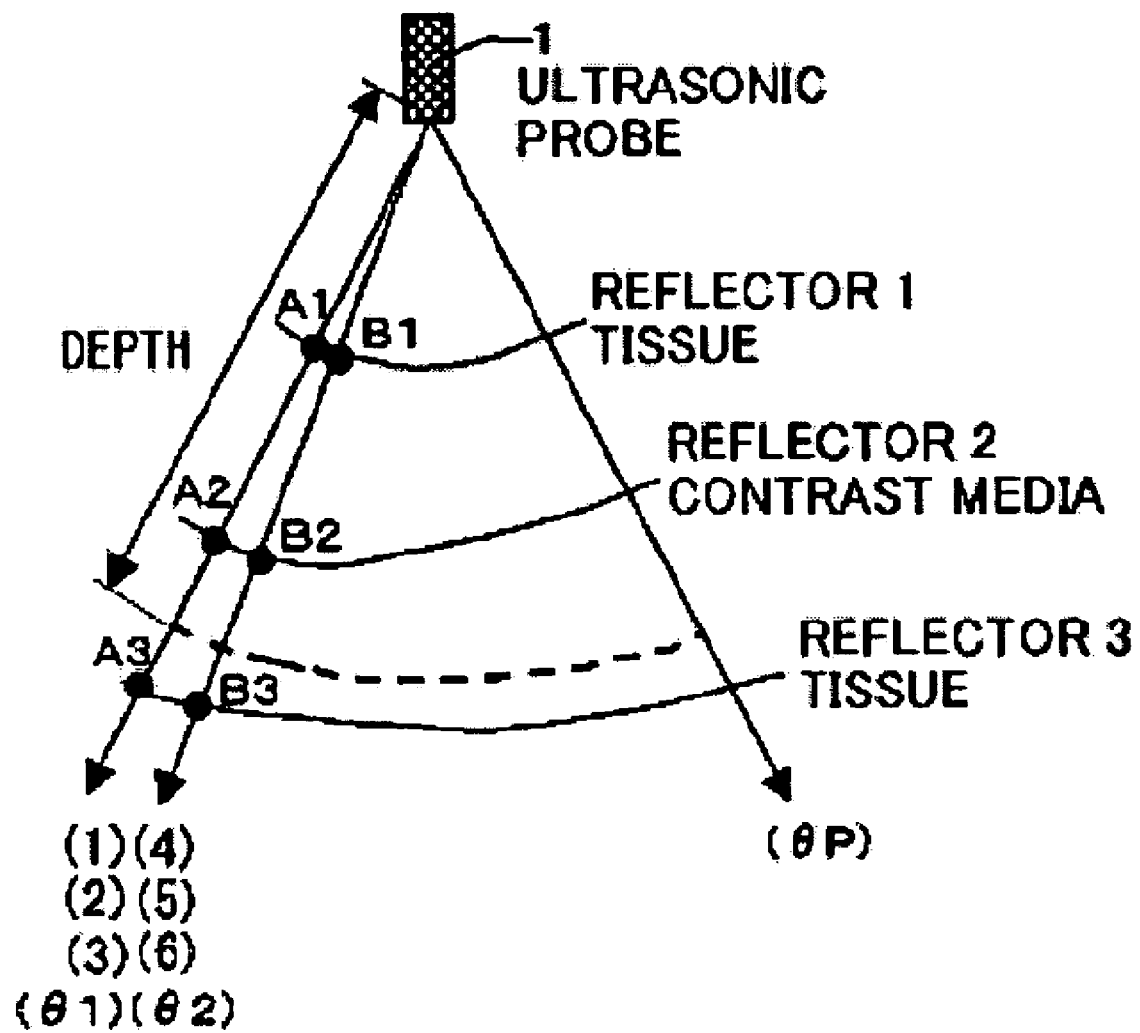
FIG. 13A and FIG. 13B are illustrations for explaining a remaining echo in the third embodiment.

A method for creating the image data will be explained in reference to FIG. 11 through FIG. 13. FIG. 12 is a flow chart of a process for creating the image data. The operator inputs the patient information, selects a contrast media display mode that is an image display mode of the third embodiment, and sets the transceiver conditions, such as the rate cycle (Step S41). The system control part 6 receives the patient information, the image display mode and the transceiver conditions from the input part 7, and reads the probe ID from the ultrasonic probe 1. The memory circuit of the system control part 6 reads the maximum receiving time Th of the received signal corresponding to probe ID and the rate cycle Tr. The CPU of the system control part 6 calculates the transmission and reception times Nx based on the above mentioned equation (3) (Step S42).

The operator injects the contrast media into a part for diagnosis of the patient, and inputs the start command signal of the image data creation by the input part 7. The inputted start command signal is sent to the system control part 6 from the input part 7, and the creation of the image data about the contrast media is started (Step S43). When the ultrasonic wave is transmitted, the rate pulse generator 11 supplies the rate pulse that determines the rate cycle Tr of the ultrasonic pulse irradiated to the patient to the transmission delay circuit 12. The transmission delay circuit 12 gives the delay time for focusing the ultrasonic wave on the predetermined depth, and the delay time for determining the first scanning direction θ1 to the rate pulse of the 1st rate section, and supplies the rate pulse to the pulsar 13. Based on the driving pulse, the pulsar 13 drives the vibration element of the ultrasonic probe 1 to irradiate the ultrasonic pulse of the center frequency fo to the patient in whom the contrast media has been injected. A part of the ultrasonic wave irradiated to the patient is reflected on border face of the internal organs where sound impedance is different, or on the tissue or the contrast media. In this case, the reflected ultrasonic wave of the center frequency 2fo is newly generated by the non linear characteristic of the patient tissue and the contrast media. That is, the reflected ultrasonic wave which reflects on the tissue or the contrast media in the patient includes the signal of the same center frequency fo as the transmitted frequency (basic component) and the signal of the center frequency 2fo (harmonics component). The reflected wave from the tissue and the contrast media of the patient is converted to the received signal by the ultrasonic probe 1, and added by the adder 25 via the preamplifier 14, A/D converter 15 and the beam former 16 (Step S6).

Among the added signals, the received signal received within the 1st rate section is sent to the waveform memory 17A of the contrast media reflection extraction part 4A (Step S44). The system control part 6 sends the controls signal to the transmitter 2 to perform transmission and reception in the first scanning direction θ1. The rate pulse generator 11 supplies the rate pulse of the 2nd rate section to the transmission delay circuit 12, which then gives the delay time for focusing the ultrasonic wave on the predetermined depth and gives the delay time for irradiating the ultrasonic wave in the first scanning direction θ1 to the rate pulse of the 2nd rate section. The rate pulse is supplied to the pulsar 13. The pulsar 13 drives the vibration element to irradiate the ultrasonic pulse in the first scanning direction θ1. A part of the transmitted ultrasonic wave is reflected on the tissue or the contrast media. However, since most contrast media is broken beforehand by the ultrasonic irradiation applied to the patient in the 1st rate section, the size of the ultrasonic reflected wave from the contrast media in the 2nd rate section is small as compared with that in the 1st rate section. On the other hand, the size of the ultrasonic reflected wave from the tissue in the 2nd rate section is almost equal to that in the 1st rate section. The reflected ultrasonic wave is received by the vibration element, and converted to the electric signal. The electric signal is amplified by the preamplifier 14 to a predetermined size and is A/D converted by the A/D converter 15. After the predetermined delay time is imposed on the digital signal by the beam former 16, addition process is performed in the adder 25.

The signal received within the 2nd rate section is stored in the waveform memory 17A of the contrast media reflection extraction part 4 (Step S45). The system control part 6 stops drive of the pulsar 13 in the 3rd section, and only reception of the ultrasonic wave is performed in the scanning direction θ1. The received signal is the remaining echo produced by the driving pulse in the 2nd rate section. The remaining echo is converted to the received signal by the vibration element and is added by the adder 25 via the preamplifier 14, the A/D converter 15 and the beam former 16. The received signal received in the 3rd rate section among the received signals added by the adder 25 is sent to the operation part 18A (Step S46). The operation part 18A reads the received signals that are received in the 1st section and 2nd section and that are stored in the waveform memory 17A. The operation part 18A extracts the contrast media signal by adding the read received signals to the received signal received in the 3rd rate section (Step S47). Subsequently, the contrast media signal extracted by the operation part 18A is sent to the filter circuit 19A. The filter characteristic of the filter circuit 19A is set to extract the harmonic component of the received signal by the system control part 6. The harmonic component of the contrast media signal extracted by the filter circuit 19A is sent to the signal processing part 5A, and is processed by the envelope detector 20 and the logarithmic converter 21 to create the image data. The image data is temporarily stored in the display memory 22 (Step S48).

When the image data in the scanning direction θ1 is created and is stored, the transmission/reception direction is incremented by Δθ, and the above-mentioned process is repeated by Δθ. That is, the process is performed in the direction θp=θ1+(p−1)Δθ, where p=2 through P. The system control part 6 creates the image data, changing the transmission and reception direction based on the delay time of the transmission delay circuit 12 and the beam former 16 (Step S44 through S50). Thus, when the image data for a single image is stored, the system control part 6 reads out the image data stored in the display memory 22 to display the image data on the CRT monitor 24 via the converter 23 (Step S51).

Figure 13B:
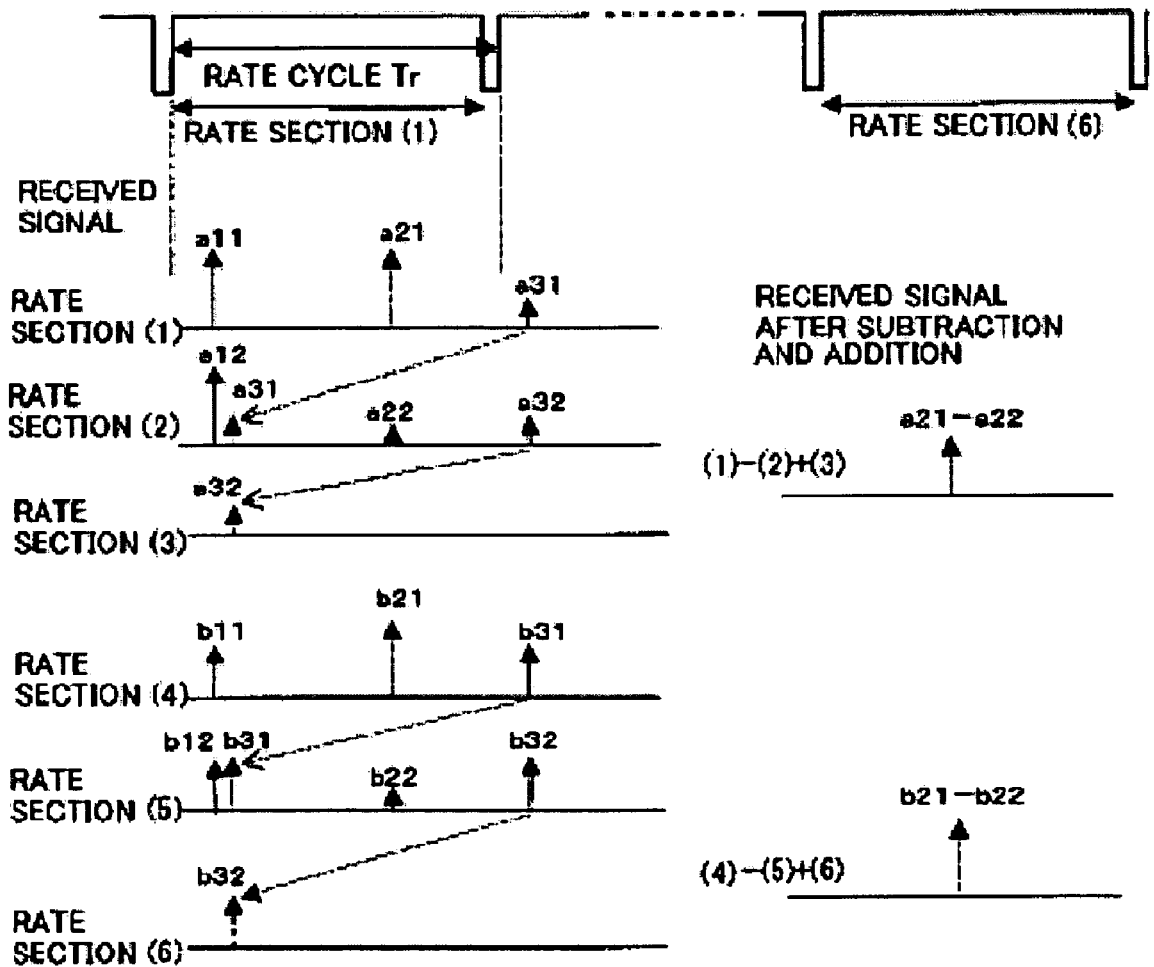

Reduction of the remaining basic component will be explained in reference to FIG. 13 and FIG. 13B. The transmission and reception is performed in the rate sections (1) though (3) in regard to the 1st direction θ1, and subsequently the transmission and reception is performed in the rate sections (4) though (6) in regard to the 2nd direction that is adjacent to the 1st direction θ1. The reflector 1 is the tissue, the reflector 2 is the contrast media and the reflector 3 is the tissue of the patient. It takes longer to perform the ultrasonic transmission and reception in regard to the reflector 3 than the rate cycle Tr. FIG. 13B shows the rate pulse for determining the irradiation timing of the ultrasonic wave, and the received signals from the reflector 1, 2 and 3 within the rate section (1) through (6). Size and polarity of the basic component are indicated as arrow. Further, FIG. 13B shows the result of addition of the basic components obtained in the rate sections (1) through (3). Also, FIG. 13B shows the result of addition of the basic components obtained in the rate sections (4) through (6). In this case, in the 1st, 2nd, 4th and 5th rate sections, transmissions and receptions are performed in the scanning directions θ1 and θ2. On the other hand, in the rate sections (3) and (6), only reception of the remaining echo is performed in the directions θ1 and θ2. That is, as shown in FIG. 13B, in the rate section (1), the transmitted ultrasonic pulse to the direction θ1 is reflected on the reflection points A1 through A3, and the basic components of a11, a21 and a31 are respectively received.

Subsequently, when the ultrasonic pulse is transmitted in the same direction θ1 in the 2nd rate section, the received signals are intensities a12, a22 and a32, where a11=a12, a31=a32 and a21≫a22. Since the ultrasonic pulse of the 2nd driving pulse is irradiated before receiving the reflected signal from the reflector A3 by the 1st driving pulse, the received signal from the reflector A3 is mixed with the reflected signal in the rate section (2). That is, in the 2nd rate section (2), the received signals that are reflected on the reflectors A1 and A2 are obtained, and the received signal that is reflected by the reflector A3 is received as well. In the 3rd section (3), the transmission of the ultrasonic wave is stopped, and only reception continues. The received signal receive in the 3rd section is the remaining echo that is not received in the 2nd rate section. The received signals received in the 1st rate section, the 2nd rate section and the 3rd rate section, are added by the adder 18 in order to reduce the tissue signal and to extract the contrast signal. In the third embodiment, the operation part 18 subtracts the received signal of the rate section (2) from the added signals in the rate section (1) and (3). Regarding the scanning directions from θ2 to θp, the contrast media signal can be appropriately extracted by a similar process.

In the third embodiment, since the contrast media signal is extracted from the received signals including the tissue signal, it is possible to display the state of the blood flow of the patient. Further, since the remaining echo of the tissue signal is reduced, the rate cycle can be technically shortened. Therefore, since the motion artifact can be reduced and the frame frequency can be increased, it is possible to obtain a ultrasonic image that has an improved real time characteristic.

Although in the above embodiment in equation (3) Ny=1, other value may be applied. For example, in a case of Ny=2, the transmissions and receptions are performed in the same direction in the rate sections (1) and (2), and the receptions are performed in the rate sections (3) and (4). The operation part 18A of the contrast media reflection extraction part 4A subtracts the added received signal of the rate sections (2) and (4) from the added signal of the rate sections (1) and (3) in order to reduce the remaining echo.

(Modification)

Figure 14A:
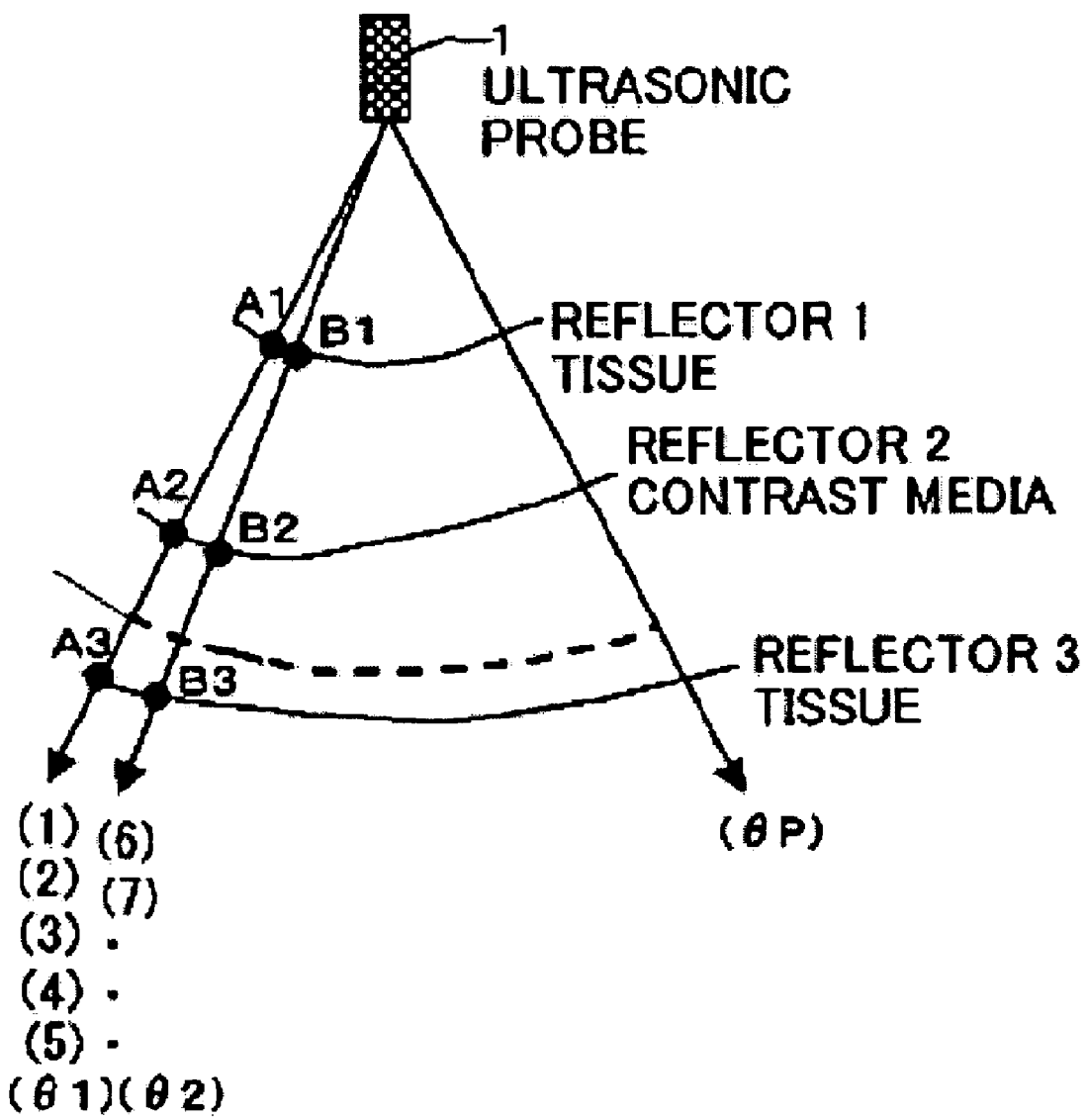
FIG. 14A and FIG. 14B are illustrations for explaining a remaining echo in a modification.
Figure 14B:
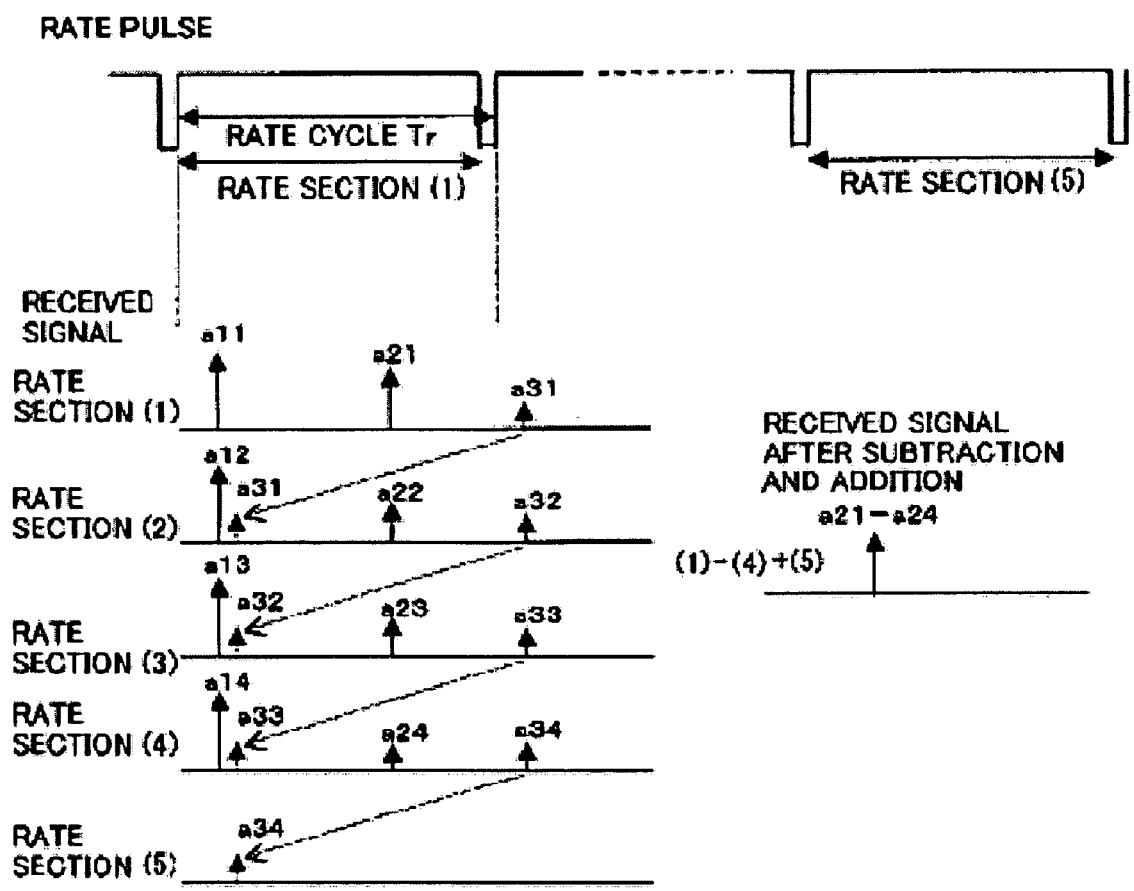

A modification will be explained with reference to FIG. 14A and FIG. 14B. In the modification, at lease three continued transmissions and receptions are performed in the same direction, and subsequently reception indicated as the above equation (3) is performed in Ny rate sections. Addition and subtraction processing are performed on the received signals acquired in the first rate section and the last rate section in order to extract the contrast media signal. Although the number of times of the transmission and the reception is four and the number of times of the reception is Ny in the modification, another number of times may be employed. In FIG. 14A, the transmissions and receptions or only reception are performed in the first scanning direction θ1 in the rate section (1) through (5), and are performed in the second scanning direction θ2 in the five rate sections after the 5th rate section (5). The reflector 1 is the tissue, the reflector 2 is the contrast media and the reflector 3 is the tissue of the patient. It takes longer to perform the ultrasonic transmission and reception in regard to the reflector 3 than the rate cycle Tr. FIG. 14B shows the rate pulse for determining the irradiation timing of the ultrasonic wave, and the received signals from the reflector 1, 2 and 3 within the rate section (1) through (5). Size and polarity of the basic component are indicated by the arrows. Further, FIG. 14B shows the result of addition and subtraction of the received signals obtained in the rate sections (1), (4) and (5). That is, the transmissions and receptions are performed in the scanning direction θ1 in the rate sections (1) through (4), and the reception is performed in the same scanning direction θ1 in the rate section (5). In the rate section (1), the ultrasonic pulse is reflected on the reflecting points A1 through A3, and the received signals of a11, a21 and a31 are obtained. Similarly, regarding the rate section (2) through (4), when the ultrasonic pulse is irradiated, the reflective ultrasonic pulses of a12 through a14 are obtained from the reflecting point A1. The reflective ultrasonic pulses of a22 through a24 are obtained from the reflecting point A2, and the reflective ultrasonic pulses of 32 through a34 are obtained from the reflecting point A3, where a11=a12=a13=a14, a31=a32=a33=a34 and a21>a22>a23>a24. The signals of the remaining echoes existing due to the transmission of the ultrasonic pulses in the rate sections (1) through (3) are mixed to the received signals received in the rate sections (2) through (4).

In the 5th rate section (5), the transmission of the ultrasonic wave is stopped, and only reception of the remaining echo by the 4th driving pulse continues. The received signals in the rate sections (1), (4) and (5) are selected, the operation part 18A adds the selected signals in order to reduce the tissue signal included in the remaining echo and to extract the contrast media signal. The operation part 18A subtracts the received signal in the rate section (4) from the added received signal in the rate sections (1) and (5). Regarding to the scanning direction θ2 through θp, processing similar to that performed to extract the contrast media signal is performed. This modification is useful in case the contrast media is not broken so much. In the modification, the addition and subtraction processing is performed to the received signals in the rate sections (1) and (4). Since the ultrasonic pulses are transmitted at three times before the rate section (4), the contrast media is quite broken, and then the contrast media signal is much smaller in the rate section (4) or later rate sections in comparison with that in the rate section (1). Therefore, it is possible to appropriately obtain the contrast media signal by the addition and the subtraction.

Fourth Embodiment

A fourth embodiment will be explained with reference to FIG. 15, FIG. 16A and FIG. 16B. The fourth embodiment has a process similar to that of the third embodiment. The transmissions and receptions or only reception is performed in the same scanning direction, and the received signals is added or subtracted to extract the contrast media signal. In the fourth embodiment, a first image data is created based on the extracted contrast media signal, and a second image data is additionally created based on the tissue data of the patient. Although the number of times of the transmission and reception is four and the number of times of reception is one in the fourth embodiment, other number of times may be employed.

(Composition of Apparatus)

Figure 15:
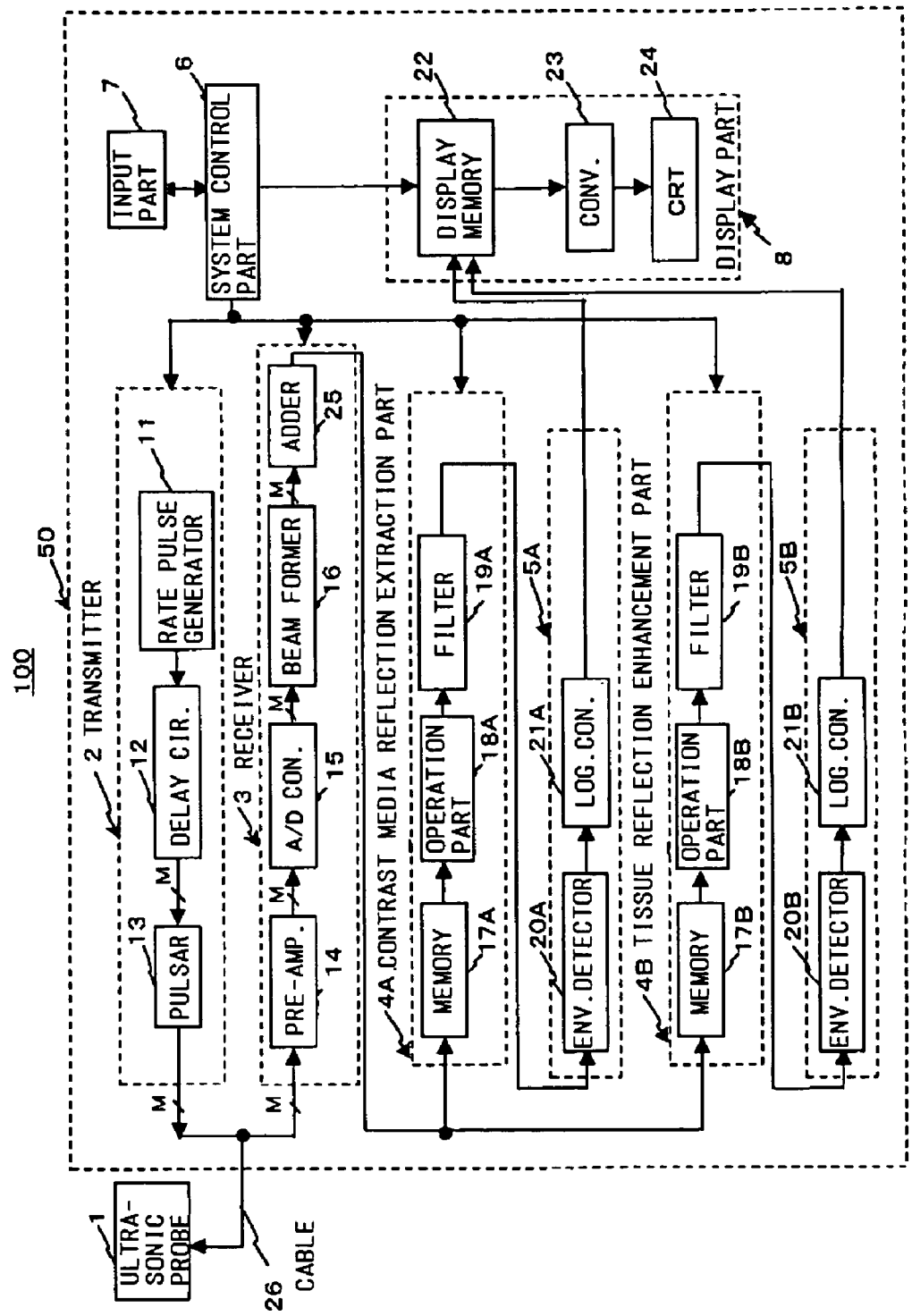
FIG. 15 is a flow chart for creating image data in a fourth embodiment.

FIG. 15 is a block diagram of an ultrasonic imaging apparatus 100. As compared to the third embodiment shown in FIG. 11, the ultrasonic imaging apparatus body 50 in the fourth embodiment further includes a tissue reflection enhancement part 4B that enhances the tissue signal and a signal processing part 5B. The tissue reflection enhancement part 4B includes a waveform memory 17B, an operation part 18B and a filter circuit 19B. The waveform memory 17B stores the received signals obtained by transmission and receptions in the rate sections (1) through (4) and the received signal obtained by reception in the rate section (5). The operation part 18B adds the received signal obtained in the rate sections (1) through (4), and subtracts the received signal obtained in the rate section (5) from the adder signal in order to enhance the tissue signal and reduce the remaining echo. The filter circuit 19B separates the basic component and the harmonic component of the contrast media signal. The filter circuit 19B may be provided prior to the waveform memory 17B.

The signal processing part 5B includes an envelope detector 20B and a logarithmic converter 21B. The signal processing part 5B processes an output signal from the tissue reflection enhancement part 4B to create the second image data.

The envelope detector 20B detects an envelope curve of the inputted digital signal. The logarithmic converter 21B relatively emphasizes a small signal by changing amplitude to a logarithm scale.

(Creation of Image Data)

A method for creating the image data will be explained in reference to FIG. 15, FIG. 16A and FIG. 16B. Similar to the third embodiment, the system control part 6 sends the control signal to the transmitter 2 and the receiver 3 in the rate sections (1) though (4), and the ultrasonic wave is transmitted to and received from the 1st scanning direction θ1. The adder 25 of the receiver 3 adds the received signals acquired from the ultrasonic vibration element. Subsequently, the added signal in each rate section is supplied to the contrast media reflection extraction part 4A and the tissue reflection enhancement part 4B, and is stored in each waveform memories 17A and 17B.

The system control part 6 performs ultrasonic reception from the scanning direction θ1 in the rate section (5), and stores the received signal from the adder 25, namely the remaining echo of the 4th rate section in the wave memories 17A and 17B. The operation part 18A of the contrast media reflection extraction part 4A performs the addition and subtraction process to the received signals in the rate sections (1), (4) and (5) to reduce the remaining echo and to extract the contrast media signal. The extracted contrast media signal is sent to the filter circuit 19A. The harmonic component of the contrast media signal is sent to the signal processing part 5A and is processed by the envelope detector 20A and the logarithmic converter 21A to create the first image data. The first image data is temporarily stored in the display memory 22. On the other hand, the operation part 18B of the tissue reflection part 4B reads and adds the signals of the rate sections (1) through (4). The operation part 18B subtracts the received signal in the rate section (5) from the added signal. By the addition and subtraction processing, S/N improves and it is possible to obtain the tissue signal and the contrast media signal without the remaining echo. When the addition and subtraction is performed, the received signal of the 5th rate section is amplified by a factor of three.

The received signal of the tissue signal and the contrast media signal extracted by the operation part 18B is sent to the filter circuit 19B. The harmonic component obtained by the filter circuit 19B is processed by the envelope detector 20B and the logarithmic converter 21B to create the second image data including the contrast media signal that is temporarily stored in the display memory of the display part 8. When the image data in the scanning direction θ1 is created and is stored, the above-mentioned process is repeated with the transmission/reception direction incremented by Δθ. That is, the process is performed in the direction θp=θ1+(p−1)Δθ, where p=2 through P. The created second image data is stored in the display memory 22 with additional information. The first image data of the contrast media and the second image data of the tissue are read out from the display memory 22, and are displayed on the CRT monitor 23 via the converter 23. It is desirable to display the first and second image data in a parallel display mode or a superimposed display mode. In the superimposed display mode, by coloring the first image data, it is easy to distinguish both image data.

The effect of the fourth embodiment will be explained in reference to FIGS. 16A and 16B. An explanation of the media contrast reflection extraction part 4A is omitted, since the explanation is similar to the third embodiment. An explanation of the tissue reflection enhancement part 4B will be explained below.

Figure 16A:
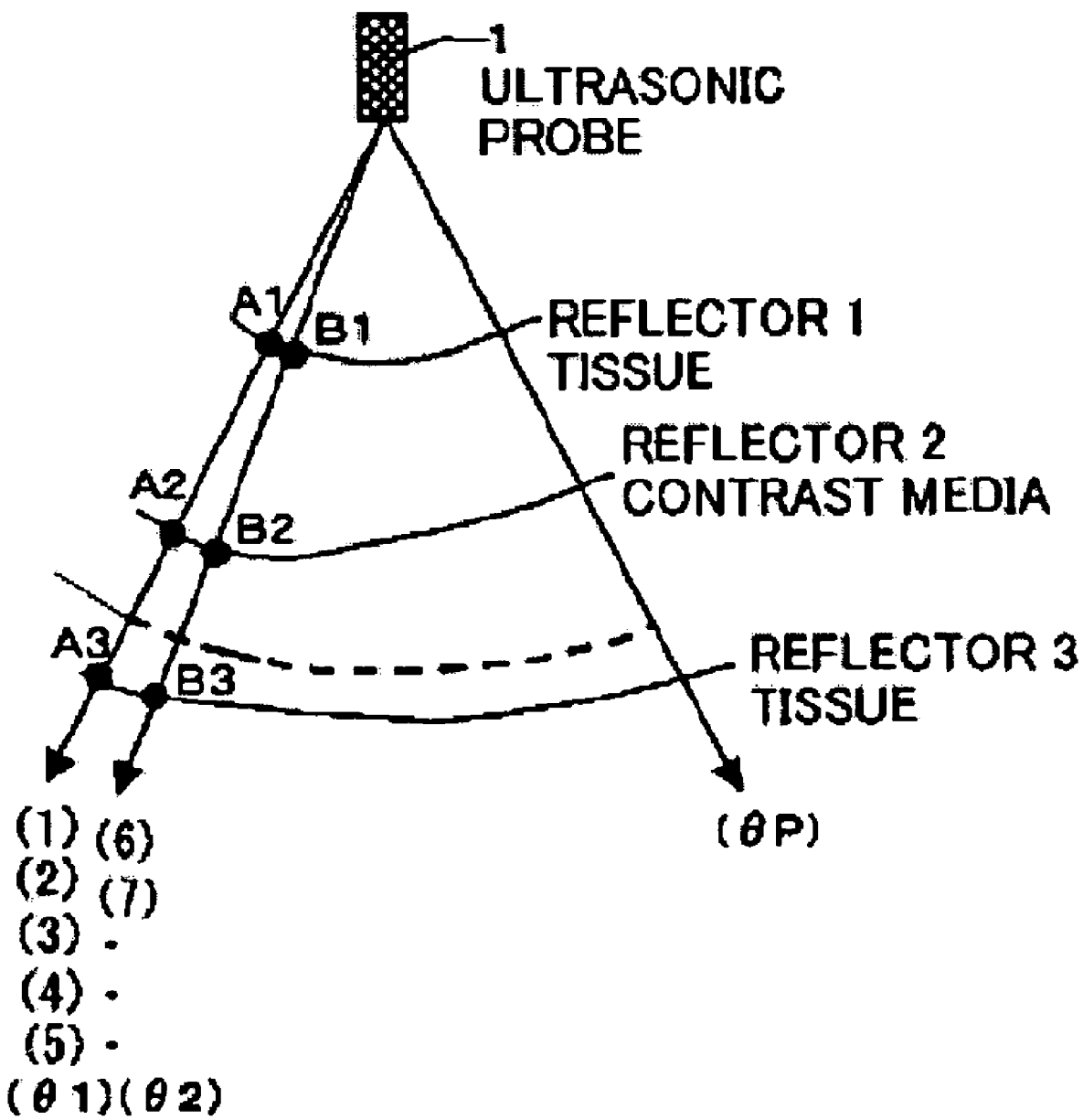
FIG. 16A and FIG. 16B are illustrations for explaining a remaining echo in the fourth embodiment.

In FIG. 16A, the transmissions and receptions or only the reception are performed in the first scanning direction θ1 in the rate section (1) through (5), and are performed in the second scanning direction θ2 in the five rate sections after the 5th rate section (5). The reflector 1 is the tissue, the reflector 2 is the contrast media and the reflector 3 is the tissue of the patient. It takes longer to perform the ultrasonic transmission and reception to the reflector 3 than the rate cycle Tr.

Figure 16B:
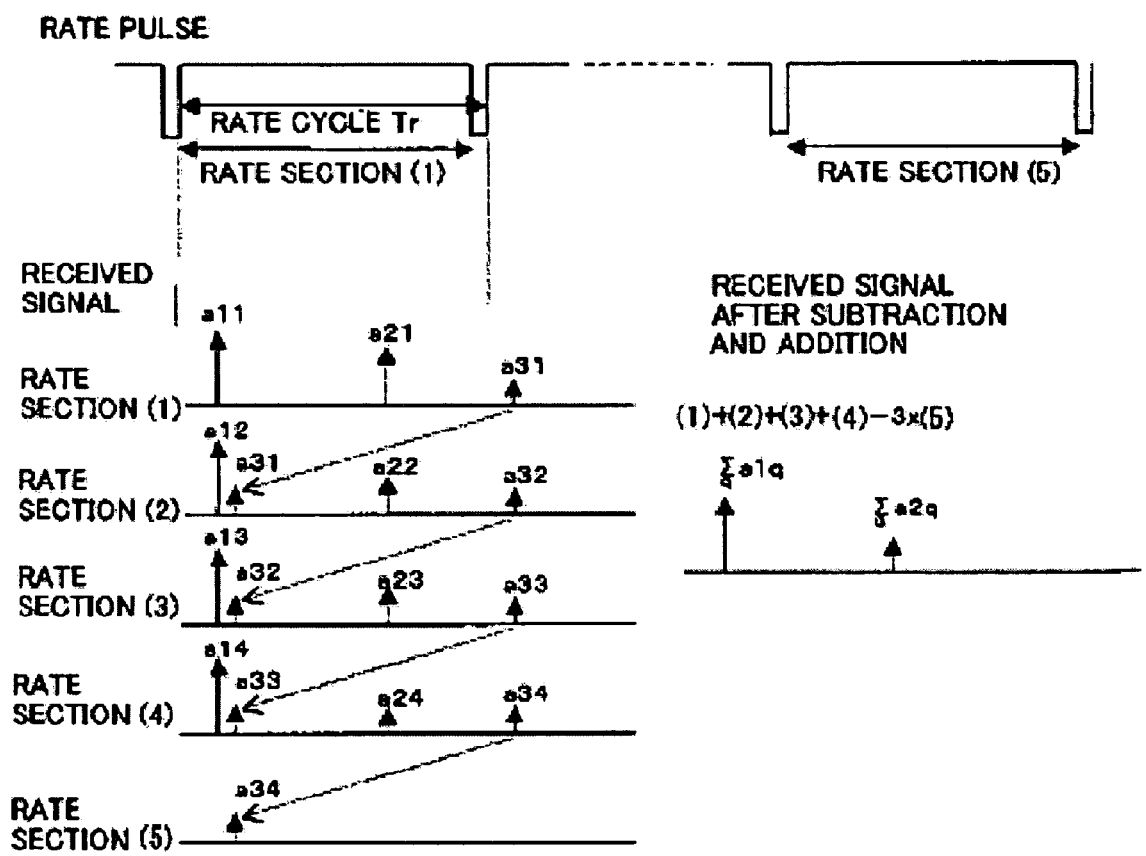

FIG. 16B shows the rate pulse for determining the irradiation timing of the ultrasonic wave, and the received signals from the reflector 1, 2 and 3 within the rate section (1) through (5). Size and polarity of the basic component are indicated by arrows. Further, FIG. 16B shows the result of addition of the received signals obtained in the rate sections (1) through (5). That is, the transmissions and receptions are performed in the scanning direction θ1 in the rate sections (1) through (4), and the reception is performed in the same scanning direction θ1 in the rate section (5). In the rate section (1), the ultrasonic pulse is reflected on the reflecting points A1 through A3, and the received signals of a11, a21 and a31 are obtained. Similarly, regarding the rate sections (2) through (4), when the ultrasonic pulse is irradiated, the reflected ultrasonic pulses a12 through a14 are obtained from the reflecting point A1, the reflected ultrasonic pulses a22 through a24 are obtained from the reflecting point A2, and the reflected ultrasonic pulses of a32 through a34 are obtained from the reflecting point A3, where a11=a12=a13=a14, a31=a32=a33=a34 and a21>a22>a23>a24. The signals of the remaining echo remained by the transmission of the ultrasonic pulses in the rate sections (1) through (3) are mixed with the received signals received in the rate sections (2) through (4).

In the 5th rate section (5), the transmission of the ultrasonic wave is stopped, and only reception of the remaining echo produced by the 4th driving pulse continues. The operation part 18A adds and subtracts the received signals in the rate sections (1) though (5) in order to improve S/N of the received signal from the tissue including the contrast media and to reduce the remaining echo. In the fourth embodiment, the received signal in the rate section (5) is amplified to three times and the amplified signal is subtracted from the added signal in the rate sections (1) through (4) in order to reduce the remaining echo.

Regarding to the scanning direction θ2 through θp, similar processing is performed to improve S/N and to reduce the remaining echo. Although the second image data includes the tissue signal and the contrast media signal, the received signals in the rate sections (2) through (4) or the rate sections (3) and (4) may be added instead of the addition of the received signals in the rate sections (1) through (4). In this case, the contrast media signal can be reduced.

In the fourth embodiment, since the tissue signal and the contrast media signal are separated, it is possible to reduce the remaining echo and to shorten the rate cycle. Therefore, the motion artifact can be reduced and in ultrasonic image having an improved real time characteristic can be obtained. Further, in the fourth embodiment, since the first image data of the contrast media and the second image data of the tissue are displayed in the parallel display mode or the superimposed display mode, it is possible easily to understand the physical relationship between the contrast media and the tissue. Although it is described that the image data is created based on the tissue signal including the contrast media in the fourth embodiment, the method may be applied to a case where the contrast media is not used, in order to improve S/N and to reduce the remaining echo.

Various modifications may be made without departing from the spirit or scope of the general inventive concept. For example, the times of transmission and reception and only reception may be other than that of the above embodiments. Although the driving pulse is stated as the positive polarized pulse in the first and second embodiments, the negative polarized pulse may be used as the first driving pulse. Otherwise, the polarity of the driving pulse may be selectable in each scanning direction. In addition, although the second order harmonic component is shown in the above embodiments, the order of the harmonic component may be more than the second. Moreover, the combination of the pulse subtraction method and the filtering method is described in the above embodiments, the filtering method may be omitted when the motion of the internal organs and the body of the patient is small. Although the polarities of the driving pulses are the same in the third and forth embodiments, the positively polarized driving pulse and the negatively polarized driving pulse may be used for the transmissions and receptions in the same scanning direction. Although the first image data or the second image data is created based on the harmonic component in the above embodiments, one of the first and second image data may be created based on the basic component. Furthermore, although the harmonic component is extracted by the filter circuit 19A and 19B in the third and fourth embodiments, a mixed component of the basic and harmonic components may be used. In this case, the filter circuit 19A and 19B may be omitted.

In the above embodiments and modifications, since the received signals obtained by the transmissions and receptions in the same direction are added or subtracted, it is possible to reduce the remaining echo without increase of the motion artifact.

What is claimed is:

1. An ultrasonic imaging apparatus, comprising:
   an ultrasonic probe including an ultrasonic vibration element configured to transmit and receive an ultrasonic wave in a scanning direction in an object;
   a transmission unit configured to make the probe transmit ultrasonic waves;
   a reception unit configured to receive reflected ultrasonic signals;
   a control unit configured to control the transmission unit such that there are three adjacent rate sections for each scan line, wherein a first transmit wave is transmitted in a first rate section, a second transmit wave is transmitted in a second rate section, and a third transmit wave is transmitted in a third rate section, the first rate section, the second rate section, and the third rate section having substantially a same length of time, wherein the length of each rate section is shorter than a time required to receive all reflected ultrasonic signals from a transmit wave transmitted in the rate section;
   an extraction unit configured to extract a signal by performing at least one of addition and subtraction of the reflected ultrasonic signals received in the second rate section and the third rate section; and
   a signal processor configured to produce image data using the signal output from the extraction unit based on the reflected ultrasonic signals received in the second and third rate sections, excluding the reflected ultrasonic signal received in the first rate section.

2. The ultrasonic imaging apparatus according to claim 1, wherein the second transmit wave has a polarity different from the first transmit wave and the third transmit wave has a polarity that is the same as the first transmit wave; and
   the extraction unit is configured to extract a signal by addition of the reflected ultrasonic signals received in the second rate section and the reflected ultrasonic signals received in the third rate section.

3. The ultrasonic imaging apparatus according to claim 1, wherein the second transmit wave and the third transmit wave have a polarity that is the same as the first transmit wave; and
   the extraction unit is configured to extract a signal by subtraction of the reflected ultrasonic signals received in the second rate section and the reflected ultrasonic signals received in the third rate section.

4. The ultrasonic imaging apparatus according to claim 1, wherein the extraction unit is configured to reduce a remaining signal attributed by the transmit wave in a different rate section from the rate section in which the remaining signal is received.

5. The ultrasonic imaging apparatus according to claim 1, wherein the extraction unit is configured to extract a harmonic signal or a contrast medium signal.

6. An ultrasonic imaging apparatus, comprising:
   an ultrasonic probe including an ultrasonic vibration element configured to transmit and receive an ultrasonic wave in a scanning direction in an object;
   a transmission unit configured to make the probe transmit ultrasonic waves;
   a reception unit configured to receive reflected ultrasonic signals;
   a control unit configured to control the transmission unit such that there are three adjacent rate sections for each scan line, wherein a first transmit wave is transmitted in a first rate section, a second transmit wave is transmitted in a second rate section, and no transmit wave is transmitted in a third rate section, the first rate section, the second rate section, and the third rate section having substantially a same length of time, wherein the length of each rate section is shorter than a time required to receive all reflected ultrasonic signals from a transmit wave transmitted in the rate section;
   an extraction unit configured to extract a signal by performing at least one of addition and subtraction of the reflected ultrasonic signals received in the first rate section, the second rate section, and the third rate section; and
   a signal processor configured to produce image data using the signal output from the extraction unit.

7. The ultrasonic imaging apparatus according to claim 6, wherein the second transmit wave has a polarity different from the first transmit wave; and
   the extraction unit is configured to extract a signal by addition of the reflected ultrasonic signals received in the first rate section, the reflected ultrasonic signals received in the second rate section, and the reflected ultrasonic signals received in the third rate section.

8. The ultrasonic imaging apparatus according to claim 6, wherein the second transmit wave has a polarity that is the same as the first transmit wave; and
   the extraction unit is configured to extract a signal by addition of the reflected ultrasonic signals received in the third rate section, and to extract a signal by subtracting the reflected ultrasonic signals received in the second rate section from the reflected ultrasonic signals received in the first rate section.

9. The ultrasonic imaging apparatus according to claim 6, wherein the extraction unit is configured to reduce a remaining signal attributed by the transmit wave in a different rate section from the rate section in which the remaining signal is received.

10. The ultrasonic imaging apparatus according to claim 6, wherein the extraction unit is configured to extract a harmonic signal or a contrast medium signal.

11. An ultrasonic imaging apparatus, comprising:
an ultrasonic probe including an ultrasonic vibration element configured to transmit and receive an ultrasonic wave in a scanning direction in an object;
a transmission unit configured to make the probe transmit ultrasonic waves;
a reception unit configured to receive reflected ultrasonic signals;
a control unit configured to control the transmission unit such that there are more than three adjacent rate sections for each scan line, wherein a transmit wave is transmitted in each of the rate sections except the last rate section of the rate sections, each of the more than three rate sections having substantially a same length of time, wherein the length of each rate section is shorter than a time required to receive all reflected ultrasonic signals from a transmit wave transmitted in the rate section;
an extraction unit configured to extract a signal by performing at least one of addition and subtraction of the reflected ultrasonic signals received in at least two of the rate sections and the last rate section; and
a signal processor configured to produce image data using the signal output from the extraction unit.

12. An method for creating image data by an ultrasonic imaging apparatus, comprising:
making a probe transmit ultrasonic waves such that there are three adjacent rate sections for each scan line, wherein a first transmit wave is transmitted in a first rate section, a second transmit wave is transmitted in a second rate section, and a third transmit wave is transmitted in a third rate section, the first rate section, the second rate section, and the third rate section having substantially a same length of time, wherein the length of each rate section is shorter than a time required to receive all reflected ultrasonic signals from a transmit wave transmitted in the rate section;
receiving reflected ultrasonic signals;
extracting a signal by performing at least one of addition and subtraction of the reflected ultrasonic signals received in the second rate section and the third rate section; and
producing image data using the signal extracted in the extracting step based on the reflected ultrasonic signals received in the second and third rate sections, excluding the reflected ultrasonic signal received in the first rate section.

13. An method for creating image data by an ultrasonic imaging apparatus, comprising:
making a probe transmit ultrasonic waves such that there are three adjacent rate sections for each scan line, wherein a first transmit wave is transmitted in a first rate section, a second transmit wave is transmitted in a second rate section, and no transmit wave is transmitted in a third rate section, the first rate section, the second rate section, and the third rate section having substantially a same length of time, wherein the length of each rate section is shorter than a time required to receive all reflected ultrasonic signals from a transmit wave transmitted in the rate section;
receiving reflected ultrasonic signals;
extracting a signal by performing at least one of addition and subtraction of the reflected ultrasonic signals received in the first rate section, the second rate section, and the third rate section; and
producing image data using the signal extracted in the extracting step.

14. An method for creating image data by an ultrasonic imaging apparatus, comprising:
making a probe transmit ultrasonic waves such that there are more than three adjacent rate sections for each scan line, wherein a transmit wave is transmitted in each of the rate sections except the last rate section of the rate sections, each of the more than three rate sections having substantially a same length of time, wherein the length of each rate section is shorter than a time required to receive all reflected ultrasonic signals from a transmit wave transmitted in the rate section;
receiving reflected ultrasonic signals;
extracting a signal by performing at least one of addition and subtraction of the reflected ultrasonic signals received in at least two of the rate sections and the last rate section; and
producing image data using the signal extracted in the extracting step.

* * * * *